United States Patent
D'amore et al.

(10) Patent No.: US 9,365,627 B2
(45) Date of Patent: Jun. 14, 2016

(54) ENDOMUCIN AS AN ANTI-INFLAMMATORY AGENT

(75) Inventors: Patricia A. D'amore, Newton, MA (US); Pablo Argüeso, Cambridge, MA (US); Alisar S. Zahr, Hillsborough, NJ (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 14/237,082

(22) PCT Filed: Aug. 6, 2012

(86) PCT No.: PCT/US2012/049730
§ 371 (c)(1),
(2), (4) Date: Sep. 25, 2014

(87) PCT Pub. No.: WO2013/022829
PCT Pub. Date: Feb. 14, 2013

(65) Prior Publication Data
US 2015/0018267 A1    Jan. 15, 2015

Related U.S. Application Data

(60) Provisional application No. 61/515,463, filed on Aug. 5, 2011.

(51) Int. Cl.
*C07K 14/47* (2006.01)
*A61K 38/17* (2006.01)
*C12N 15/11* (2006.01)
*A61K 48/00* (2006.01)

(52) U.S. Cl.
CPC ............. *C07K 14/47* (2013.01); *A61K 38/1709* (2013.01); *C12N 15/11* (2013.01); *A61K 48/005* (2013.01); *C12N 2799/022* (2013.01)

(58) Field of Classification Search
CPC ...................................................... C07K 14/47
See application file for complete search history.

(56) References Cited

U.S. PATENT DOCUMENTS

2005/0261185 A1* 11/2005 Martijn et al. .................. 514/12

OTHER PUBLICATIONS

Liu et al., 2001, Human Endomucin Is an Endothelial Marker, Biochemical and Biophysical Research Communications, 288: 129-136.*
Alcaide et al. "Neutrophil Recruitment under Shear Flow: It's All about Endothelial Cell Rings and Gaps." *Microcirculation.* 16.1(2009):43-57.
dela Paz et al. "Arterial Versus Venous Endothelial Cells." *Cell Tissue Res.* 335.1(2009):5-16.
GenBank Accession No. AAF76295.1, Jun. 15, 2000.
GenBank Accession No. NM_016242.3, Jul. 3, 2011.
Kinoshita et al. "Identification of Human Endomucin-1 and -2 as Membrane-Bound O-sialoglycoproteins with Anti-Adhesive Activity." *FEBS Lett.* 499.1-2(2001):121-126.
Morgan et al. "Biochemical Characterization and Molecular Cloning of a Novel Endothelial-Specific Sialomucin." *Blood.* 93.1(1999):165-175.
Sumiyoshi et al. "Antiadhesive Character of Mucin O-Glycans at the Apical Surface of Corneal Epithelial Cells." *Invest. Ophthalmol. Vis. Sci.* 49.1(2008):197-203.

* cited by examiner

*Primary Examiner* — Amber D Steele
(74) *Attorney, Agent, or Firm* — Mintz Levin Cohn Ferris Glovsky and Popeo, P.C.

(57) ABSTRACT

The invention provides compositions and methods for utilizing endomucin as an anti-inflammatory agent.

18 Claims, 22 Drawing Sheets

$I = a\sqrt{\eta\rho}(2\pi f)^3 \text{dynes/cm}^2$ siScramble             siEndomucin-1

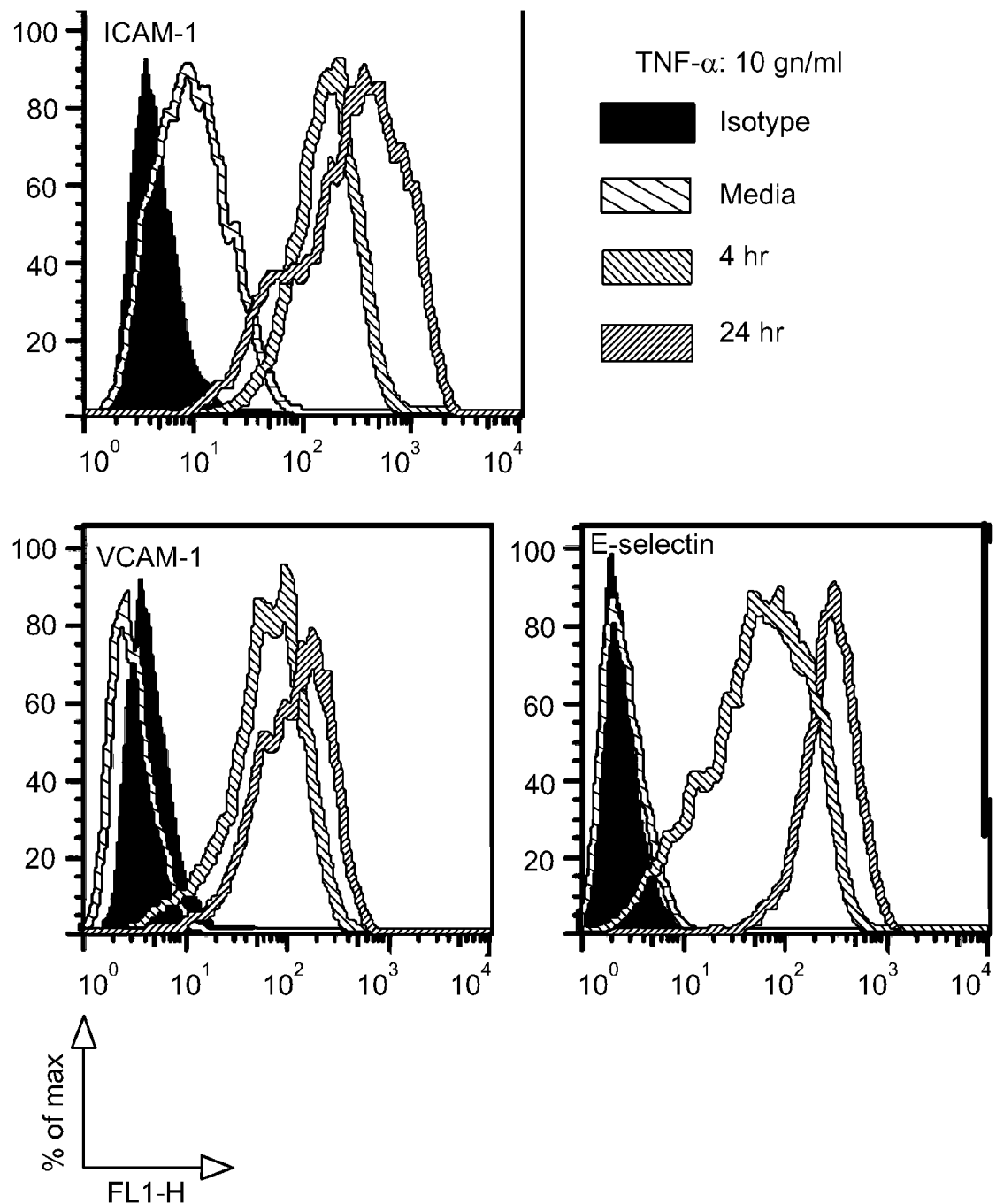

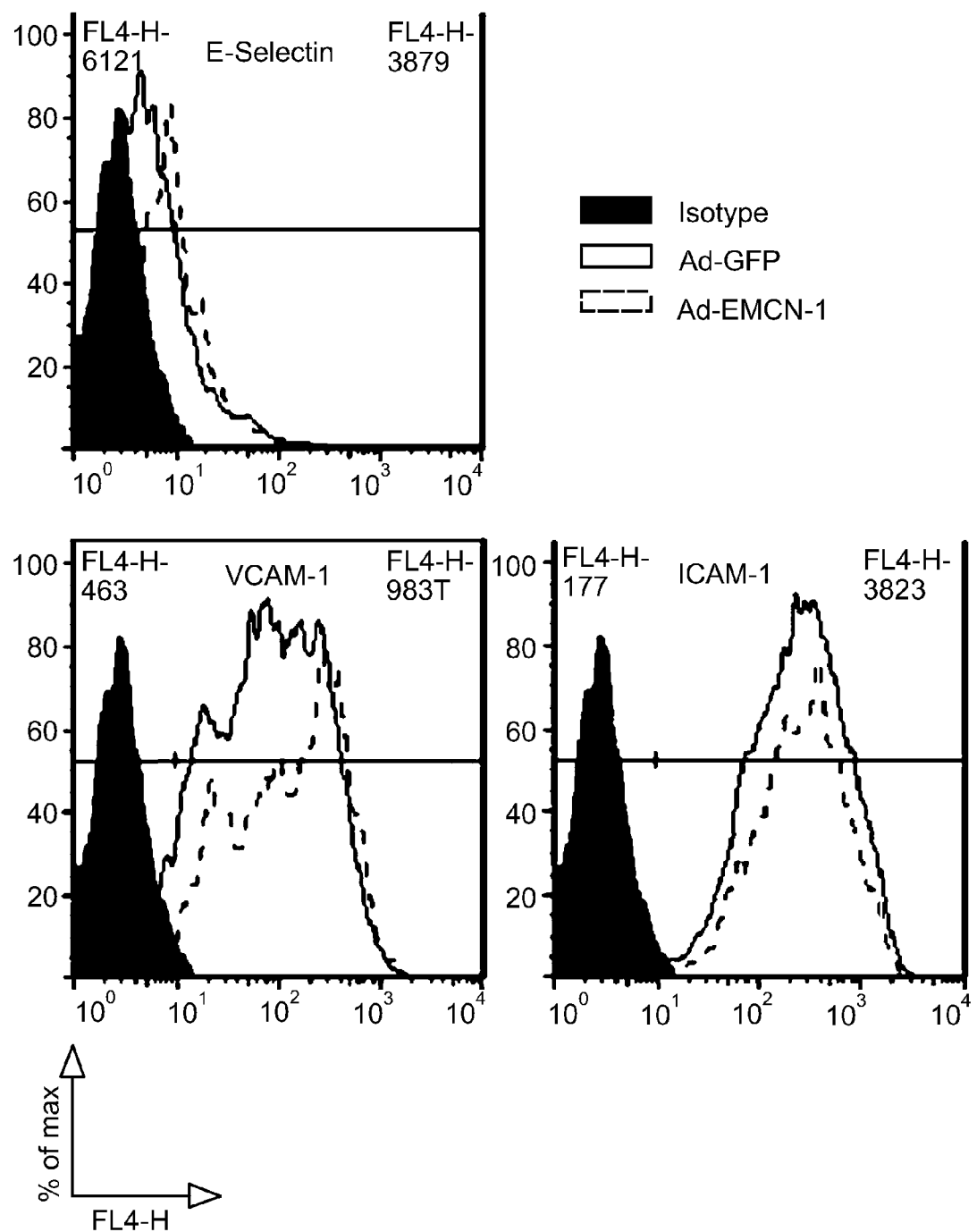

SEQUENCE LISTING

```
<160> NUMBER OF SEQ ID NOS: 2

<210> SEQ ID NO 1
<211> LENGTH: 4047
<212> TYPE: DNA
<213> ORGANISM: Homo sapiens

<400> SEQUENCE: 1
gggagtgtgt gtatttcctc ccgttcttta tcagagcccc caaaataagt aggaatgggc      60
agtggctatt cacattcact acaccttttc catttgctaa taaggccctg ccaggctggg     120
agggaattgt ccctgcctgc ttctggagaa agaagatatt gacaccatct acgggcacca     180
tggaactgct tcaagtgacc attctttttc ttctgcccag tatttgcagc agtaacagca     240
caggtgtttt agaggcagct aataattcac ttgttgttac tacaacaaaa ccatctataa     300
caacaccaaa cacagaatca ttacagaaaa atgttgtcac accaacaact ggaacaactc     360
ctaaaggaac aatcaccaat gaattactta aaatgtctct gatgtcaaca gctacttttt     420
taacaagtaa agatgaagga ttgaaagcca caaccactga tgtcaggaag aatgactcca     480
tcatttcaaa cgtaacagta acaagtgtta cacttccaaa tgctgtttca acattacaaa     540
gttccaaacc caagactgaa actcagagtt caattaaaac aacagaaata ccaggtagtg     600
ttctacaacc agatgcatca ccttctaaaa ctggtacatt aacctcaata ccagttacaa     660
ttccagaaaa cacctcacag tctcaagtaa taggcactga gggtggaaaa aatgcaagca     720
cttcagcaac cagccggtct tattccagta ttattttgcc ggtggttatt gctttgattg     780
taataacact ttcagtattt gttctggtgg gtttgtaccg aatgtgctgg aaggcagatc     840
cgggcacacc agaaaatgga aatgatcaac ctcagtctga taaagagagc gtgaagcttc     900
ttaccgttaa gacaatttct catgagtctg gtgagcactc tgcacaagga aaaaccaaga     960
actgacagct tgaggaattc tctccacacc taggcaataa ttacgcttaa tcttcagctt    1020
ctatgcacca agcgtggaaa aggagaaagt cctgcagaat caatcccgac ttccatacct    1080
gctgctggac tgtaccagac gtctgtccca gtaaagtgat gtccagctga catgcaataa    1140 tttgatgaa tcaaaagaa ccccgggct ctcctgttct ctcacattta aaaattccat    1200
tactccattt acaggagcgt tcctaggaaa aggaatttta ggaggagaat ttgtgagcag    1260
```

```
tgaatctgac agcccaggag gtgggctcgc tgataggcat gactttcctt aatgtttaaa    1320
gttttccggg ccaagaattt ttatccatga agactttcct acttttctca gtgttcttat    1380
attacctact gttagtattt attgtttacc actatgttaa tgcagggaaa agttgcacgt    1440
gtattattaa atattaggta gaaatcatac catgctactt tgtacatata agtattttat    1500
tcctgctttc gtgttacttt taataaataa ctactgtact caatactcta aaaatactat    1560
aacatgactg tgaaaatggc aatgttattg tcttcctata attatgaata ttttggatg    1620 gattattaga atacatgaac tcactaatga aaggcatttg taataagtca gaaagggaca    1680
tacgattcac atatcagact gttaggggga gagtaattta tcagttcttt ggtcttcta    1740 tttgtcattc atactatgtg atgaagatgt aagtgcaagg gcatttataa cactatactg    1800
cattcattaa gataatagga tcatgatttt tcattaactc atttgattga tattatctcc    1860
atgcattttt tatttctttt agaaatgtaa ttatttgctc tagcaatcat tgctaacctc    1920
tagtttgtag aaaatcaaca ctttataaat acataattat gatattattt ttcattgtat    1980
cactgttcta aaaataccat atgattatag ctgccactcc atcaggagca aattcttctg    2040
ttaaaagcta actgatcaac cttgaccact ttttgacat gtgagatcaa agtgtcaagt    2100
tggctgaggt ttttggaaa gctttagaac taataagctg ctggtggcag ctttgtaacg    2160
tatgattatc taagctgatt ttgatgctaa attatcttag tgatctaagg ggcagtttag    2220
tgaagatgga atcttgtatt taaaatagcc ttttaaaatt tgttttgtgg tgatgtattt    2280
tgacaacttc catctttagg agtatataa tcaccttgat tttagtttcc tgatgtttgg    2340
actatttata atcaaggaca ccaagcaagc ataagcatat ctatatttct gactggtgtc    2400
tctttgagaa ggatgggaag tagaaaaaaa aaaagaaag aaggaaagg aagagaggag    2460 agaagaaggc agggatctcc actatgtatg ttttcacttt agaactgttg agcccatgct    2520
taattttaat ctagaagtct ttaaatggtg agacagtgac tggagcatgc caatcagaga    2580
gcatttgtct tcagaaaaaa aaaaaatctg agtttgagac tagcctggcc aacatgttga    2640
aaccccatat ctactaaaaa tacaaaaatt agcctggtgt ggtggcgcac gcctgtagtc    2700
ccagctactc tggagcctga ggaacgtgaa tcgcttgaac ccagaagaca gaggttgcag    2760
tgagctgaga tggcactatt gcactccagc ctgggtgaca cagcaagact ctgtctcaaa    2820 aaaaaaaaa aaaaaagga aaaaaagaa agaaagaaag tcccagcaca cctagataat    2880
ttaccgagct cttcagcaaa aaccatgtta catacagcat attccaaaga aatgaactct    2940
tctgcaattt aaattataag taatatgtta ttttggatcc tagagaaacc attttctcta    3000
catttcatga gcatggttag aaaagagttt acaagaatta ggaagaggga acaattttaa    3060
tggtcagaaa agaataaaat ttattctagt tcaagaagtg cacacaaaga atatgcatta    3120
atctaacaac tatgagatta aatctttcaa aaaggtcaaa ggaggattga aagtttaca    3180 gagatgtcca cggcatttta tatcaatctc aaaggtaagg tctgcatttt tataaaccaa    3240
cttaaacttc tgttgagata ggatattttg ttttcaagcc aaaattacca ttaatcaaat    3300
atgttttaat tatctgattt agatgatcta cttttatgc ctggcttact gtaagttttt    3360
tattctgata cacagttcaa acatcattgc aacaaagaag tgcctgtatt tagatcaaag    3420
gcaagacttt ctatgtgttt gttttgcata ataatatgaa tataatttaa gtctatcaat    3480
agtcaaaaca taaacaaaag ctaattaact ggcactgttg tcacctgaga ctaagtggat    3540
gttgttggct gacatacagg ctcagccagc agagaaagaa ttctgaattc cccttgctga    3600
actgaactat tctgttacat atggttgaca aatctgtgtg ttatttcttt tctacctacc    3660
```

-continued

```
atatttaaat ttatgagtat caaccgagga catagtcaaa ccttcgatga tgaacattcc    3720
tgattttttg cctgattatt ctctgttgag ctctacttgt ggtcattcaa gattttatga    3780
tgttgaaagg aaaagtgaat atgacctta aaaattgtat tttgggtgat gatagtctca     3840
ccactataaa actgtcaatt attgcctaat gttaaagata tccatcattg tgattaatta    3900
aacctataat gagtattctt aatggagaat tcttaatgga tggattatcc cctgatcttt    3960
tctttaaaat ttctctgcac acacaggact tctcatttc caataaatgg gtgtactctg    4020
ccccaatttc tagggaaaaa aaaaaaa                                       4047
```

<210> SEQ ID NO 2
<211> LENGTH: 261
<212> TYPE: PRT
<213> ORGANISM: Homo sapiens

<400> SEQUENCE: 2

```
Met Glu Leu Leu Gln Val Thr Ile Leu Phe Leu Leu Pro Ser Ile Cys
1               5                  10                  15

Ser Ser Asn Ser Thr Gly Val Leu Glu Ala Ala Asn Ser Leu Val
                20                  25                  30

Val Thr Thr Thr Lys Pro Ser Ile Thr Thr Pro Asn Thr Glu Ser Leu
            35                  40                  45

Gln Lys Asn Val Val Thr Pro Thr Gly Thr Thr Pro Lys Gly Thr
        50                  55                  60

Ile Thr Asn Glu Leu Leu Lys Met Ser Leu Met Ser Thr Ala Thr Phe
65                  70                  75                  80

Leu Thr Ser Lys Asp Glu Gly Leu Lys Ala Thr Thr Thr Asp Val Arg
                85                  90                  95

Lys Asn Asp Ser Ile Ile Ser Asn Val Thr Val Thr Ser Val Thr Leu
            100                 105                 110

Pro Asn Ala Val Ser Thr Leu Gln Ser Ser Lys Pro Lys Thr Glu Thr
        115                 120                 125

Gln Ser Ser Ile Lys Thr Thr Glu Ile Pro Gly Ser Val Leu Gln Pro
    130                 135                 140

Asp Ala Ser Pro Ser Lys Thr Gly Thr Leu Thr Ser Ile Pro Val Thr
145                 150                 155                 160

Ile Pro Glu Asn Thr Ser Gln Ser Gln Val Ile Gly Thr Glu Gly Gly
                165                 170                 175

Lys Asn Ala Ser Thr Ser Ala Thr Ser Arg Ser Tyr Ser Ser Ile Ile
            180                 185                 190

Leu Pro Val Val Ile Ala Leu Ile Val Ile Thr Leu Ser Val Phe Val
        195                 200                 205

Leu Val Gly Leu Tyr Arg Met Cys Trp Lys Ala Asp Pro Gly Thr Pro
    210                 215                 220

Glu Asn Gly Asn Asp Gln Pro Gln Ser Asp Lys Glu Ser Val Lys Leu
225                 230                 235                 240

Leu Thr Val Lys Thr Ile Ser His Glu Ser Gly Glu His Ser Ala Gln
                245                 250                 255

Gly Lys Thr Lys Asn
            260
```

ENDOMUCIN AS AN ANTI-INFLAMMATORY AGENT

RELATED APPLICATIONS

This application is a national stage application, filed under 35 U.S.C. §371, of International Application No. PCT/US2012/049730, filed Aug. 6, 2012, which claims the benefit of priority under 35 U.S.C. §119(e) to U.S. Provisional Application No. 61/515,463, filed Aug. 5, 2011, which are incorporated herein by reference in their entireties.

INCORPORATION-BY-REFERENCE OF SEQUENCE LISTING

The contents of the text file named "36770-520N01US_ST25.txt", which was created on Feb. 4, 2014 and is 8 KB in size, are hereby incorporated by reference in their entirety.

FIELD OF THE INVENTION

This invention relates generally to the field of vascular biology and inflammation.

BACKGROUND OF THE INVENTION

Endothelial cell-leukocyte interactions have been a topic of intense investigation for the last several decades. From the viewpoint of the role of endothelial cells, most focus has been on the expression, regulation, and function of pro-adhesive molecules. Prior to the invention described herein, little attention has been paid to the mechanisms involved in the suppression or attenuation of leukocyte adhesion to the endothelium by anti-adhesive molecules. As such, there is a pressing need to develop new targets for the manipulation of leukocyte adhesion during inflammation.

SUMMARY OF THE INVENTION

The invention is based on the surprising discovery that an endothelial-specific glycoprotein, endomucin-1 (EMCN-1), attenuates neutrophil-endothelial cell interactions. Described herein is the use of EMCN-1 as a therapeutic target for the manipulation of leukocyte adhesion during inflammation in a subject. The subject is preferably a mammal in need of such treatment, e.g., a subject that has been diagnosed with inflammation (e.g., ocular inflammation) or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Inflammation is part of the complex biological response of vascular tissues to disease or to potentially harmful stimuli, such as pathogens, damaged cells, or irritants. Thus, subjects characterized as at risk of or suffering from an inflammatory disorder, e.g., an ocular inflammatory disorder, include those subjects that comprise a disease/disorder or have been exposed to such harmful stimuli or are at risk for exposure to such stimuli. Characteristics of inflammation include swelling, redness, heat/warmth, pain, loss of function, or itchiness of the affected area, e.g., as a result of injury or disease. For example, a subject is identified as suffering from an ocular inflammatory disorder by detecting a sign or symptom selected from the group consisting of epithelial overexpression of an inflammatory cytokine, vascular hyperplasia or thickening of lid margin, neovascularization of lid margin or corneal periphery, increase of leukocytes at an ocular or adnexal tissue, or overexpression of a matrix metalloprotease at an ocular or adnexal tissue. Ocular surface inflammation is also characterized by changes in mucous (increased during allergy and reduced during dry eye) and tear secretion, and compromised corneal epithelial barrier.

The invention provides a specific molecule, EMCN-1 that inhibits or disrupts the adhesion of neutrophils to the activated endothelium during inflammation, as well as block basal neutrophil adhesion in non-inflammatory conditions. Described herein are methods of inducing EMCN-1 expression on the vascular system, or a part thereof, and use of recombinant EMCN-1 and vectors genetically engineered to over express EMCN-1 on endothelial cells. Also provided are methods of treating inflammatory diseases that involve adhesion of leukocytes to endothelial cells in capillaries and post-capillary venules. EMCN-1 disrupts and prevents neutrophil-endothelial cell interactions, and thus the propagation of inflammation in the tissue.

Specifically, the invention provides methods of reducing inflammation in a subject. Optionally, a subject with an inflammatory disease is identified, e.g., by detecting redness, swelling, heat/warmth of a tissue of the subject or detecting an increase in pro-inflammatory mediators such as interferon gamma (IFN-γ), interleukin 8 (IL-8), leukotriene B4, nitric oxide, prostaglandins, tumor necrosis factor alpha (TNF-α), or IL-1. The level of EMCN on endothelial cells in a tissue in the subject is therapeutically increased. An increase in EMCN reduces the adhesion of the leukocytes to the endothelial cells in the tissue. Optionally, the expression of EMCN is upregulated. Alternatively, EMCN is therapeutically upregulated in a subject at high risk for inflammation. In one example, human EMCN-1 is upregulated. For example, basal neutrophil adhesion is reduced in non-inflammatory conditions.

For example, a purified EMCN polypeptide is administered to the subject. In some cases, the purified EMCN polypeptide comprises the amino acid sequence of SEQ ID NO: 2. Alternatively, a purified nucleic acid encoding the EMCN is administered to the subject. In some cases, the purified nucleic acid encoding the EMCN comprises the sequence of SEQ ID NO: 1.

The inflammatory disease may be any inflammatory disease characterized by leukocyte adhesion to the endothelium. The inflammatory disease is an ocular inflammatory disease selected from the group consisting of dry eye disease, uveitis, diabetic retinopathy, and endophthalmitis. In another aspect, the inflammatory disease is a non-ocular inflammatory disease selected from the group consisting of psoriasis, rheumatoid arthritis, inflammatory bowel disease, asthma, transplant rejection disease, vasculitis, and an autoimmune disease.

The endothelial cells comprise vascular endothelial cells. Exemplary leukocytes include neutrophils, eosinophils, basophils, lymphocytes, monocytes, macrophages, and dendritic cells.

Preferably, the adhesion of leukocytes to endothelial cells is reduced at least 5%, e.g., at least 10%, 20%, 30%, 40%, 50%, 60%, 70%, 80%, 90%, or 100%. For example, the adhesion of leukocytes to endothelial cells is reduced at least 2 fold, e.g., at least 3 fold, at least 4 fold, or at least 5 fold.

The invention also provides methods for reducing inflammation in a subject. A vector, e.g., an adenovirus vector, comprising a nucleic acid construct comprising a polynucleotide sequence for EMCN-1 operably linked to a promoter such that the EMCN-1 is over-expressed. Overexpression of EMCN-1 reduces the adhesion of leukocytes to endothelial cells in the subject.

Preferably, the overexpression of EMCN-1 reduces inflammatory cell infiltration to an anatomical site. For example, overexpression of EMCN-1 reduces CD45+ cell infiltration to a tissue.

EMCN-1 is administered as deoxyribonucleic acid, ribonucleic acid, or a protein. For example, EMCN-1 is administered via gene or protein drug delivery. Exemplary drug delivery vehicles include polymeric micelles, liposomes, lipoprotein-based drug carriers, nano-particle drug carriers, dendrimers, etc. Optionally, the delivery is targeted. For example, antibodies to proadhesive molecules linked to recombinant EMCN-1 are delivered.

In one aspect, EMCN-1 is injected into a tissue such as the eye or the skin. For example, the EMCN-1 is injected intravitreally into the eye, subcutaneously into skin, or intravenously into the vein for systemic administration. Alternatively, the composition is administered topically. For example, the form of a composition of the above methods is a solid, a paste, an ointment, a gel, a liquid (e.g., an eye drop), an aerosol, a mist, a polymer, a film, an emulsion, or a suspension.

All polynucleotides and polypeptides of the invention are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides the nucleic acid molecule, the two phrases can be used interchangeably.

A "heterologous promoter", when operably linked to a nucleic acid sequence, refers to a promoter which is not naturally associated with the nucleic acid sequence.

The terms "express" and "over-express" are used to denote the fact that, in some cases, a cell useful in the method herein may inherently express some of the factor that it is to be genetically altered to produce, in which case the addition of the polynucleotide sequence results in over-expression of the factor. That is, more protein is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to reduce or prevent inflammation (e.g., ocular inflammation) in a mammal Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DETAILED DESCRIPTION

The invention is based on the surprising discovery that an endothelial-specific glycoprotein, endomucin-1 (EMCN-1), attenuates neutrophil-endothelial cell interactions. Described herein is the use of EMCN-1 as a new therapeutic target for the manipulation of leukocyte adhesion during inflammation in a subject. The subject is preferably a mammal in need of such treatment, e.g., a subject that has been diagnosed with inflammation (e.g., ocular inflammation) or a predisposition thereto. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The invention described herein is a fundamentally different approach from existing technologies because it takes advantage of the anti-adhesive properties of EMCN-1. Prior to the invention described herein, anti-inflammatory methods targeted pro-inflammatory cytokines, ligands, or receptors via blocking antibodies. Actemra, a monoclonal antibody that inhibits interleukin-6 receptor, was the first humanized antibody developed to treat chronic inflammatory diseases. Other examples include anti-tumor necrosis factor-alpha (TNF-alpha) therapies such as Enbrel®, Remicade®, Humira®, Cimzia®, and Simponi®. Continued use of Humira® and Remicade® can result in side effects, such as increased risk of fungal infections, tuberculosis, and rare cancer of white cells. In addition, TNF-alpha blockers are not effective orally, and must given as subcutaneous injections or intravenously, which may lead to patient discomfort.

The invention provides a specific molecule, EMCN-1 that inhibits or disrupts the adhesion of neutrophils to the activated endothelium during inflammation. Described herein are methods of inducing EMCN-1 expression on the vascular system, or a part thereof, and use of recombinant EMCN-1 and vectors genetically engineered to over express EMCN-1 on endothelial cells.

Figure 1:
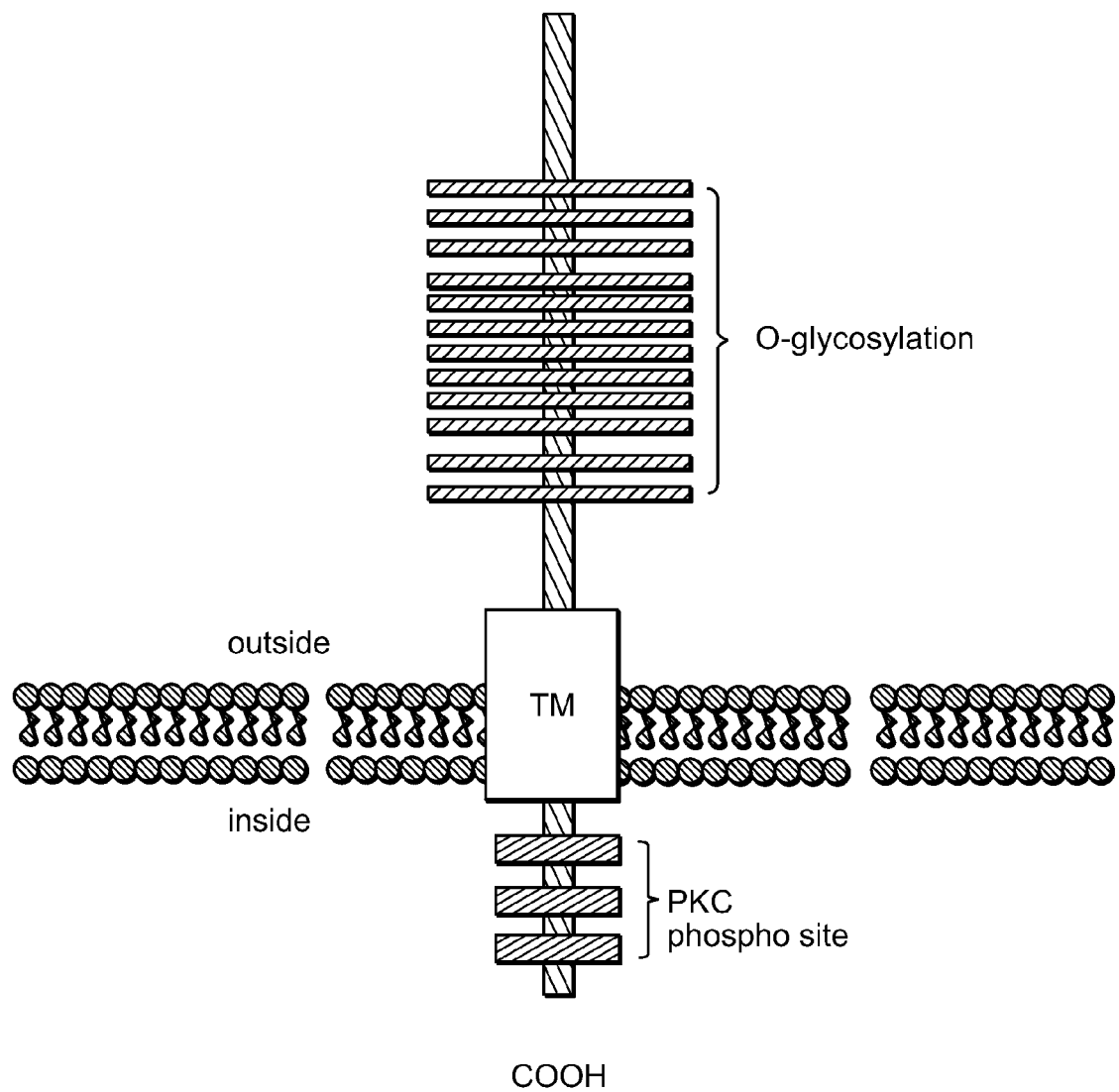
FIG. 1 is a schematic showing a type I transmembrane protein.
Figure 2:
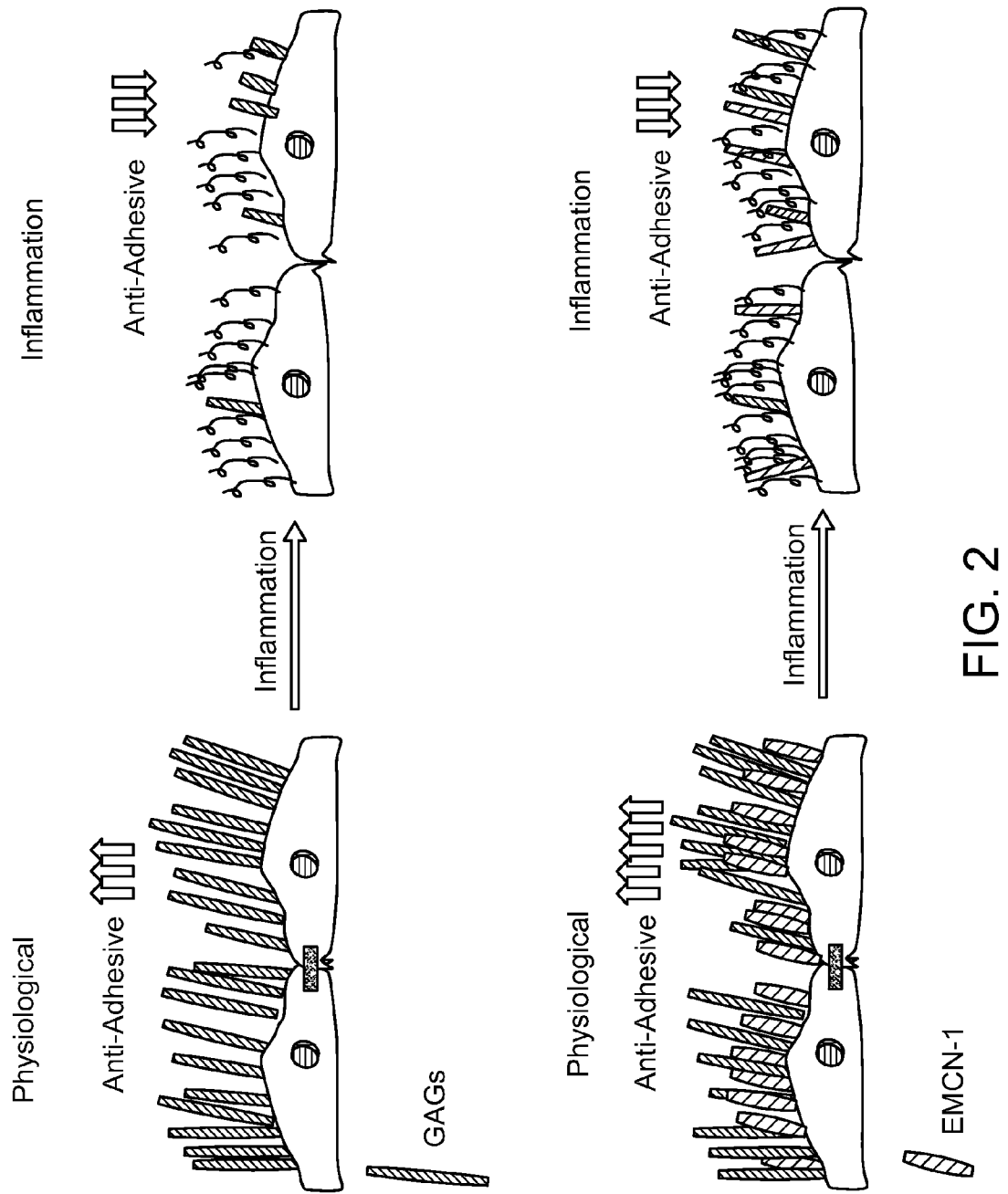
FIG. 2 is a schematic illustrating the role of endomucin-1 (EMCN-1) in inflammation.

Human EMCN-1 is a type 1-membrane O-sialoglycoprotein found on the luminal surface of venous and capillary endothelium (Morgan et al., 1999 Blood, 93:165-75; dela Paz and D'Amore, 2009 Cell Tissue Res, 335 (1):5-16). EMCN-1 is comprised of 248 amino acids with a high content of serine and threonine residues (35%) (Morgan et al., 1999 Blood, 93(1): 165-75). These residues located in the extracellular domain are sites for O-glycosylation. The extended rod-like structure of the protein is shown in FIG. 1. These features, similar to other mucins, have the ability to act as a repulsive barrier to cell-cell interactions via steric hindrance and or charge repulsion (Sumiyoshi et al., 2008 Invest Ophthalmol Vis Sci, 49(1): 197-203). EMCN-1 was first cloned in 1999, but prior to the invention described herein, little was known on its biological function. O-glycosylated proteins can regulate cell adhesion (Sumiyoshi et al., 2008 Invest Ophthalmol Vis Sci, 49(1):197-203), and overexpression of EMCN-1 in non-endothelial cells reduces focal adhesion assembly and suppresses matrix interactions (Morgan et al., 1999 Blood, 93(1): 165-75; Kinoshita et al., 2001 FEBS Lett, 499(1-2): 121-6). Although EMCN-1 is not expressed on arteries, EMCN-1 is apically expressed on endothelial cells in veins and post-capillary venules, which are sites of inflammation (FIG. 3; Alcaide et al., 2009 Microcirculation, 16(1): 43-57). The description of the sequence and structure of EMCN in each of the references in the preceding paragraph is incorporated herein by reference As described in detail below, EMCN-1 is an anti-adhesive glycoprotein important in regulating leukocyte-endothelial cell interactions. Post-capillary venous endothelium is the major site of leukocyte recruitment and extravasation during inflammation. Expression of leukocyte adhesion molecules at the endothelial surface modulates rolling, adhesion, and migration of leukocytes. Prior to the invention described herein, the interaction between leukocytes and EMCN-1 at the cell surface under physiological and inflammatory conditions had not been investigated. As described in detail below, EMCN-1 attenuates neutrophil-endothelial cell interactions under both physiological and inflammatory conditions. The model of inflammation describe herein is provided in FIG. 2.

The results presented herein demonstrate that cell surface EMCN-1 provides an anti-adhesive character to the endothelial glycocalyx, regulating the adhesion of neutrophils to the endothelium during quiescent and inflammatory conditions. As described in detail below, over expression of EMCN-1 in the eye protects the neural retina and ciliary body from CD45+ mediated infiltration.

The nucleic acid and amino acid sequences of full length human EMCN-1 is provided below. However, the invention also comprises polypeptides and nucleic acid fragments, so long as they exhibit the desired biological activity (i.e., anti-inflammatory activity) of the full length polypeptides and nucleic acid, respectively. A nucleic acid fragment of almost any length is employed. For example, illustrative polynucleotide segments with total lengths of about 4,000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 225, about 100, about 50, about 25, or about 10-12 amino acids in length (including all intermediate lengths) are included in many implementations of this invention.

Fragments are at least less than 261 amino acids (full length). For example, a fragment includes the signal peptide of EMCN-1, e.g., amino acids 1-18 of full length EMCN-1. Alternatively, a fragment comprises amino acids 19-261 of full length EMCN-1. Exemplary amino acid fragments include those that comprise the extracellular domain of EMCN-1, i.e., amino acids 19-190. For example, a fragment of EMCN-1 comprises amino acids 70-181; amino acids 70-89; or amino acids 173-181 of full length EMCN-1. Suitable fragments also include those that comprise the transmembrane of EMCN-1, i.e., amino acids 191-211. Other suitable fragments include those that comprise the cytoplasmic domain of EMCN-1, i.e., amino acids 212-261. For example, a fragment of EMCN-1 comprises amino acid 237 of full length EMCN-1. In some cases, exemplary fragments include a glycosylated amino acid at position 19, 28, 98, 104, 164, or 178 of full length EMCN-1. In other cases, exemplary fragments include a phosphorylated amino acid at position 70, 76, 80, 173, 180, 181, or 237 of full length EMCN-1.

The sequence of human endomucin-1 nucleic acid (SEQ ID NO: 1) is provided below (GenBank Accession Number: NM_016242.3 (GI:229576879), incorporated herein by reference). The signal peptide is encoded by nucleic acids 180-233. The mature peptide is encoded by nucleic acids 234-962.

```
                                                (SEQ ID NO: 1)
   1   gggagtgtgt gtatttcctc ccgttcttta tcagagcccc
       caaaataagt aggaatgggc 61   agtggctatt cacattcact acaccttttc catttgctaa
       taaggccctg ccaggctggg 121   agggaattgt ccctgcctgc ttctggagaa agaagatatt
       gacaccatct acgggcacca 181   tggaactgct tcaagtgacc attcttttc ttctgcccag
       tatttgcagc agtaacagca 241   caggtgtttt agaggcagct aataattcac ttgttgttac
       tacaacaaaa ccatctataa 301   caacaccaaa cacagaatca ttacagaaaa atgttgtcac
       accaacaact ggaacaactc 361   ctaaaggaac aatcaccaat gaattactta aaatgtctct
       gatgtcaaca gctactttt 421   taacaagtaa agatgaagga ttgaaagcca caaccactga
       tgtcaggaag aatgactcca 481   tcatttcaaa cgtaacagta acaagtgtta cacttccaaa
       tgctgtttca acattacaaa 541   gttccaaacc caagactgaa actcagagtt caattaaaac
       aacagaaata ccaggtagtg 601   ttctacaacc agatgcatca ccttctaaaa ctggtacatt
       aacctcaata ccagttacaa 661   ttccagaaaa cacctcacag tctcaagtaa taggcactga
       gggtggaaaa aatgcaagca 721   cttcagcaac cagccggtct tattccagta ttatttttgcc
       ggtggttatt gctttgattg 781   taataacact ttcagtattt gttctggtgg gtttgtaccg
       aatgtgctgg aaggcagatc 841   cgggcacacc agaaaatgga aatgatcaac ctcagtctga
       taaagagagc gtgaagcttc 901   ttaccgttaa gacaattct catgagtctg gtgagcactc
       tgcacaagga aaaaccaaga 961   actgacagct tgaggaattc tctccacacc taggcaataa
       ttacgcttaa tcttcagctt 1021   ctatgcacca agcgtggaaa aggagaaagt cctgcagaat
       caatcccgac ttccatacct 1081   gctgctggac tgtaccagac gtctgtccca gtaaagtgat
       gtccagctga catgcaataa 1141   tttgatgaa tcaaaaagaa ccccgggct ctcctgttct
       ctcacattta aaaattccat 1201   tactccattt acaggagcgt tcctaggaaa aggaattta
       ggaggagaat ttgtgagcag 1261   tgaatctgac agcccaggag gtgggctcgc tgataggcat
       gactttcctt aatgtttaaa 1321   gttttccggg ccaagaattt ttatccatga agctttcct
       acttttctca gtgttcttat 1381   attacctact gttagtattt attgtttacc actatgttaa
       tgcagggaaa agttgcacgt
```

```
1441  gtattattaa atattaggta gaaatcatac catgctactt
      tgtacatata agtattttat 1501  tcctgctttc gtgttacttt taataaataa ctactgtact
      caatactcta aaaatactat 1561  aacatgactg tgaaaatggc aatgttattg tcttcctata
      attatgaata tttttggatg 1621  gattattaga atacatgaac tcactaatga aaggcatttg
      taataagtca gaaagggaca 1681  tacgattcac atatcagact gttaggggga gagtaattta
      tcagttcttt ggtctttcta 1741  tttgtcattc atactatgtg atgaagatgt aagtgcaagg
      gcatttataa cactatactg 1801  cattcattaa gataatagga tcatgatttt tcattaactc
      atttgattga tattatctcc 1861  atgcattttt tatttctttt agaaatgtaa ttatttgctc
      tagcaatcat tgctaacctc 1921  tagtttgtag aaaatcaaca ctttataaat acataattat
      gatattattt ttcattgtat 1981  cactgttcta aaaataccat atgattatag ctgccactcc
      atcaggagca aattcttctg 2041  ttaaaagcta actgatcaac cttgaccact tttttgacat
      gtgagatcaa agtgtcaagt 2101  tggctgaggt ttttggaaa gctttagaac taataagctg
      ctggtggcag cttttgtaacg 2161  tatgattatc taagctgatt ttgatgctaa attatcttag
      tgatctaagg ggcagtttag 2221  tgaagatgga atcttgtatt taaaatagcc ttttaaaatt
      tgttttgtgg tgatgtattt 2281  tgacaacttc catctttagg agttatataa tcaccttgat
      tttagtttcc tgatgtttgg 2341  actatttata atcaaggaca ccaagcaagc ataagcatat
      ctatatttct gactggtgtc 2401  tctttgagaa ggatgggaag tagaaaaaaa aaaaagaaag
      aaaggaaagg aagagaggag 2461  agaagaaggc agggatctcc actatgtatg ttttcacttt
      agaactgttg agcccatgct 2521  taatttaat ctagaagtct ttaaatggtg agacagtgac
      tggagcatgc caatcagaga 2581  gcatttgtct tcagaaaaaa aaaaaatctg agtttgagac
      tagcctggcc aacatgttga 2641  aacccatat ctactaaaaa tacaaaaatt agcctggtgt
      ggtggcgcac gcctgtagtc 2701  ccagctactc tggagcctga ggaacgtgaa tcgcttgaac
      ccagaagaca gaggttgcag 2761  tgagctgaga tggcactatt gcactccagc ctgggtgaca
      cagcaagact ctgtctcaaa 2821  aaaaaaaaa aaaaaagga aaaaaagaa agaagaaag
      tcccagcaca cctagataat 2881  ttaccgagct cttcagcaaa aaccatgtta catacagcat
      attccaaaga aatgaactct 2941  tctgcaattt aaattataag taatatgtta ttttggatcc
      tagagaaacc atttctcta 3001  catttcatga gcatggttag aaaagagttt acaagaatta
      ggaagaggga acaattttaa
```

```
3061  tggtcagaaa agaataaaat ttattctagt tcaagaagtg
      cacacaaaga atatgcatta 3121  atctaacaac tatgagatta aatctttcaa aaaggtcaaa
      ggaggattga gaagtttaca 3181  gagatgtcca cggcatttta tatcaatctc aaaggtaagg
      tctgcatttt tataaaccaa 3241  cttaaacttc tgttgagata ggatattttg ttttcaagcc
      aaaattacca ttaatcaaat 3301  atgttttaat tatctgattt agatgatcta cttttatgc
      ctggcttact gtaagttttt 3361  tattctgata cacagttcaa acatcattgc aacaaagaag
      tgcctgtatt tagatcaaag 3421  gcaagacttt ctatgtgttt gttttgcata ataatatgaa
      tataatttaa gtctatcaat 3481  agtcaaaaca taaacaaaag ctaattaact ggcactgttg
      tcacctgaga ctaagtggat 3541  gttgttggct gacatacagg ctcagccagc agagaaagaa
      ttctgaattc cccttgctga 3601  actgaactat tctgttacat atggttgaca aatctgtgtg
      ttatttcttt tctacctacc 3661  atatttaaat ttatgagtat caaccgagga catagtcaaa
      ccttcgatga tgaacattcc 3721  tgattttttg cctgattatt ctctgttgag ctctacttgt
      ggtcattcaa gattttatga 3781  tgttgaaagg aaaagtgaat atgacccttta aaaattgtat
      tttgggtgat gatagtctca 3841  ccactataaa actgtcaatt attgcctaat gttaaagata
      tccatcattg tgattaatta 3901  aacctataat gagtattctt aatggagaat tcttaatgga
      tggattatcc cctgatcttt 3961  tcttaaaat ttctctgcac acacaggact tctcattttc
      caataaatgg gtgtactctg 4021  ccccaatttc tagggaaaaa aaaaaaa
```

The sequence of human endomucin-1 protein (SEQ ID NO: 2) is provided below (GenBank Accession Number: AAF76295.1 (GI:8547215), incorporated herein by reference). The signal peptide is underlined. The remaining amino acids set forth the sequence of the mature peptide.

```
                                           (SEQ ID NO: 2)
  1   mellqvtilf llpsicssns tgvleaanns lvvtttkpsi
      ttpnteslqk nvvtpttgtt 61   pkgtitnell kmslmstatf ltskdeglka tttdvrknds
      iisnvtvtsv tlpnaystlq 121   sskpktetqs siktteipgs vlqpdaspsk tgtltsipvt
      ipentsqsqv igteggknas 181   tsatsrsyss iilpvviali vitlsvfvlv glyrmcwkad
      pgtpengndq pqsdkesvkl 241   ltvktishes gehsaqgktk n
```

EXAMPLE 1

Venous and Capillary Endothelium Expresses EMCN-1 In Vivo

Figure 3A:
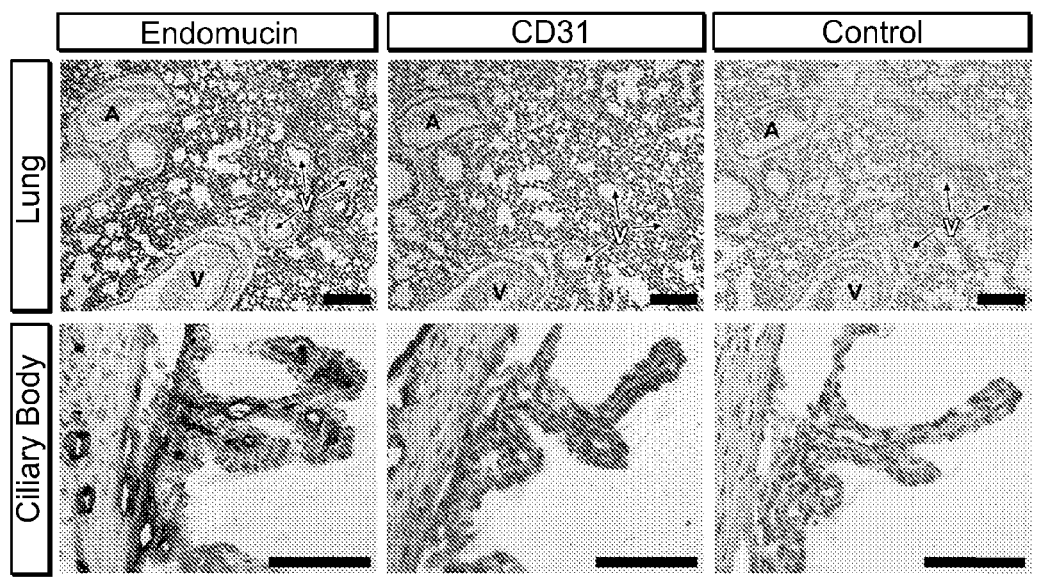
FIG. 3 is a series of photomicrographs showing venous and capillary (but not arterial endothelium) expresses EMCN-1 in vivo. (A) Tissues were dissected from adult C5BL6 mice, fixed in 4% PFA, frozen in OCT, and cut into 10 mm sections. Anti-EMCN-1 was used to identify venous ECs. EMCN-1 was localized to veins and capillaries of mouse lung. CD31 was localized to veins, capillaries, and arteries of mouse lung. "A" and "V" denote arteries and veins, respectively. EMCN-1 co-localizes with CD31+ endothelial cells in ciliary body. (B) In paraffin sections of normal human skin, EMCN-1 (green) was localized on the apical surface of a venule nuclei (red).
Figure 3B:
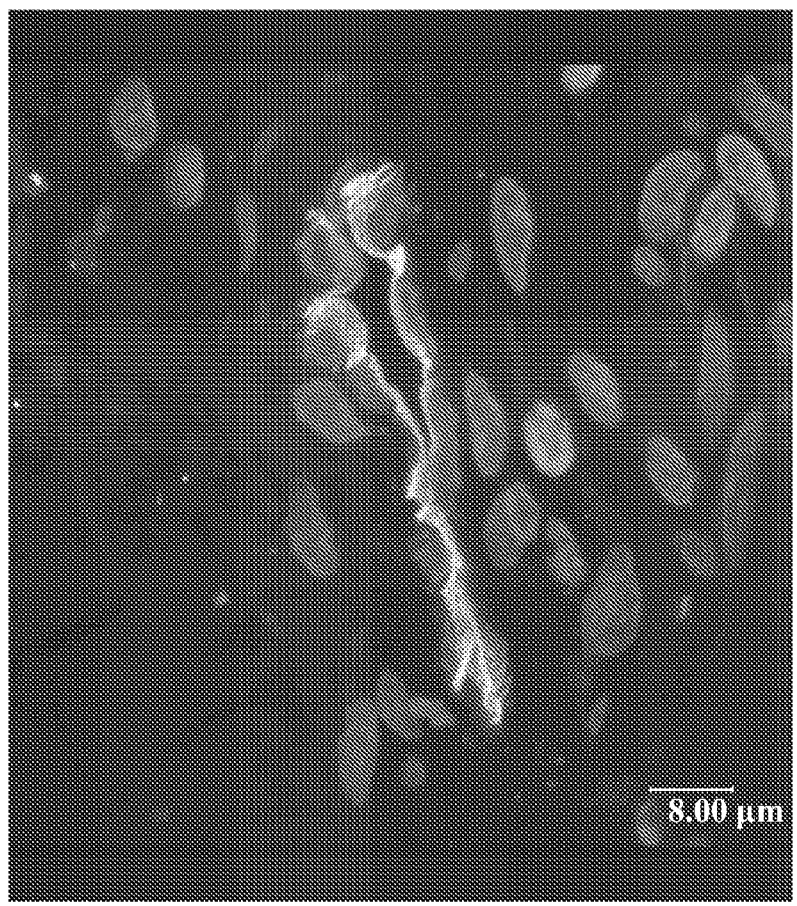

Venous and capillary (but not arterial) endothelium expresses EMCN-1 in vivo. To determine expression patters on EMCN-1, tissues were dissected from adult C5BL6 mice, fixed in 4% PFA, frozen in OCT, and cut into 10 mm sections. Anti-EMCN-1 was used to identify venous ECs. EMCN-1 was localized to veins and capillaries of mouse lung (FIG. 3A). CD31 was localized to veins, capillaries, and arteries of mouse lung. EMCN-1 co-localizes with CD31+ endothelial cells in ciliary body. As shown in FIG. 3B, paraffin sections of normal human skin EMCN-1 (green) was localized on the apical surface of a venule nuclei (red). "A" and "V" denote arteries and veins, respectively.

EXAMPLE 2

High Shear Stress Down-Regulates EMCN-1 mRNA Expression and Surface Localization in HUVEC Cell Culture. Primary human umbilical vein endothelial cells (HUVEC) were used as the in vitro cell model. HUVEC were cultured in EBM-2 medium containing 20% FBS and used from passages 2-6.

In vitro inflammation model. EMCN-1 biosynthesis in confluent HUVEC was analyzed following TNF-alpha (10 ng/ml, 25 ng/ml) treatment. After 4 and 24 hrs of treatment, protein and cell surface expression of EMCN-1 and pro-adhesive molecules were determined using a biotinylation-based assay and FACS.

Figure 4:
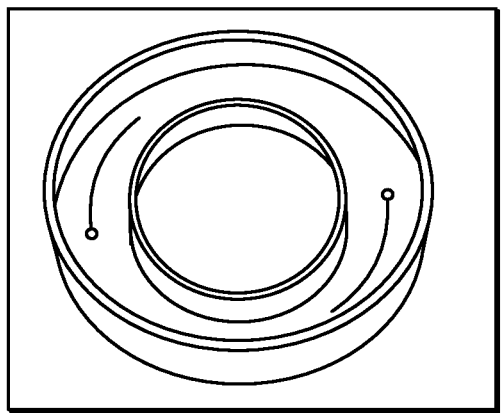
FIG. 4 is a schematic and a photograph illustrating the dishes used for the in vitro shear stress model.
Figure 4:
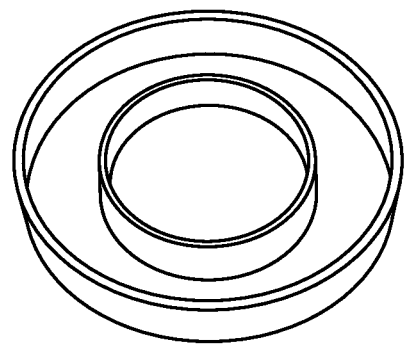

In vitro shear stress model. HUVEC are seeded into the center of the inner dish (FIG. 4). At confluence, media is changed to 0.5% FBS and the dish is placed on an orbital shaker and exposed to shear stress (calculated using equation below), arterial shear stress (10 dyn/cm$^2$) and venous shear stress (1.5 dyn/cm$^2$) for 24 hrs. mRNA and cell surface protein expression were determined at 24 hrs and compared to static conditions.

Cell-cell interaction assay. A parallel plate flow chamber was used to study the interaction between HUVEC and purified human neutrophils. HUVEC mono-layers were sheared 1.5 to 0.5 dyn/cm$^2$ in the presence of neutrophils. The number of rolling and firmly adhered neutrophils was quantified per area in each field recorded.

In vivo model of inflammation. BL6 mice were injected with TNF-alpha (20 ng/μL) into the vitreous of the left eye. At 24 hrs, injected eyes were enucleated and prepped for lysates of the neural retina and anterior segment (iris and ciliary body).

Figure 5A:
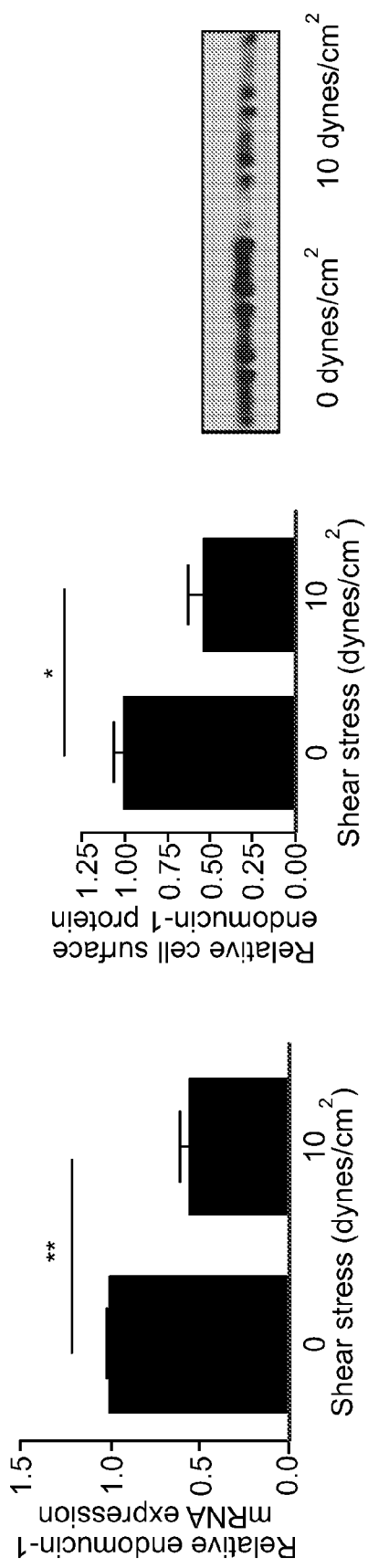
FIG. 5 is a series of bar charts and photomicrographs showing that shear stress (SS) regulates messenger ribonucleic acid (mRNA) expression and surface localization of EMCN-1 in human umbilical vein endothelial cells (HUVEC). EMCN-1 is regulated by shear stress and is mediated by Krueppel-like factor 2 (KLF2). HUVECs were seeded in 6-well culture dishes and exposed to shear stress for 24 hr. (A) EMCN-1 is down regulated in HUVEC by high levels shear stress (10 dyne/cm$^2$) compared to static conditions determined by mRNA and cell surface biotinylation, respectively. Inset is a representative gel illustrating decreased biosynthesis of EMCN-1 protein by shear stress-induced HUVEC compared to static control cells as measured by western blot. (B) Venular-like shear stress of 1.5 dynes/cm$^2$ has no effect on mRNA and cell surface protein levels. Inset shows representative gel of EMCN-1 biosynthesis in HUVEC exposed to venular shear stress compared to static controls. (C) Real-time polymerase chain reaction (PCR) analysis of EMCN-1 in Ad-Ctrl vs. Ad-KLF-2 (Ad-KLF4 or Ad-KLF2/4) infected HUVEC. (D) Real-time PCR analysis of EMCN-1 in response to small interfering RNA (siRNA) oligonucleotides directed against KLF2 for 48 hr followed by exposure to static or flow conditions for an additional 24 hr. Relative expression of EMCN-1 measured by real-time PCR and normalized to glyceraldehyde 3-phosphate dehydrogenase (GAPDH) mRNA levels. The amount of complementary deoxyribonucleic acid (cDNA) was normalized using GAPDH levels and quantified using a standard curve for EMCN-1. Relative cell surface expression of EMCN-1 normalized to static controls. Biotinylation results represent one experiment performed in triplicate. *p<0.05, **p<0.01.
Figure 5B:
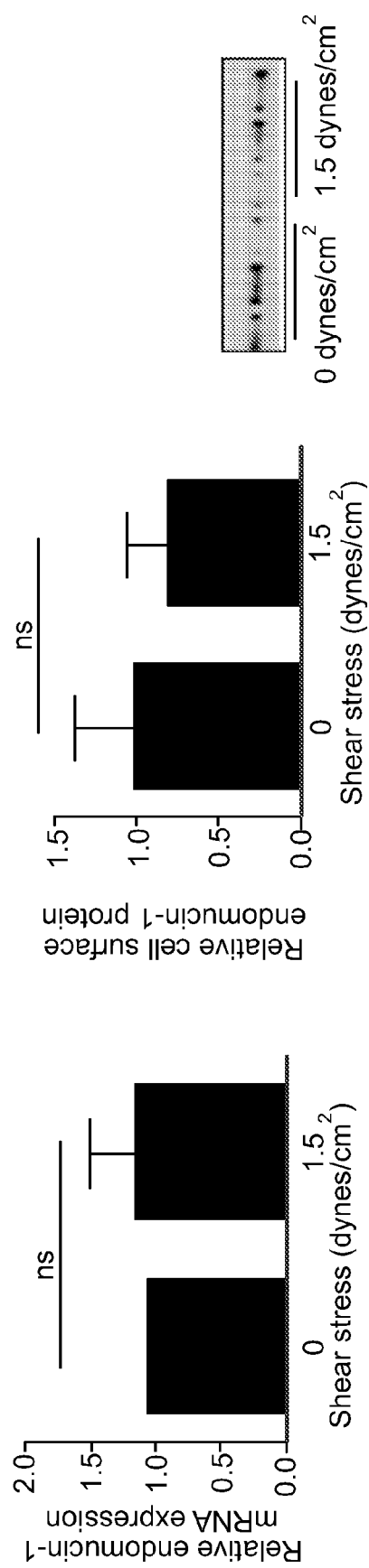
Figure 5C:
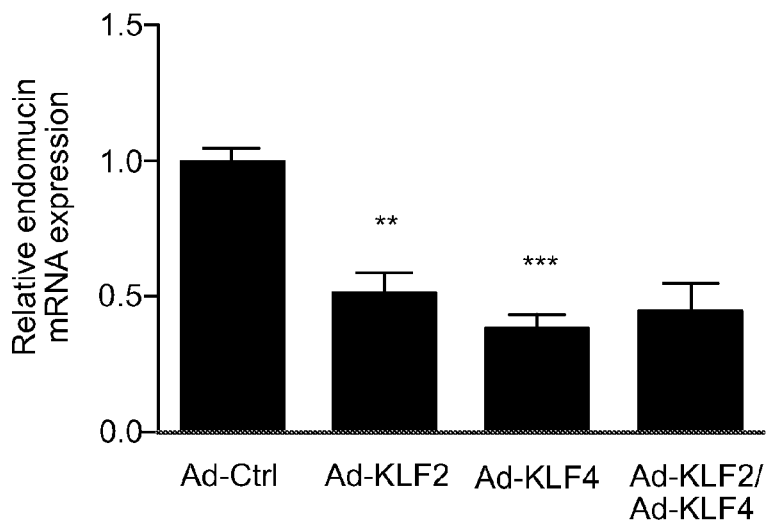
Figure 5D:
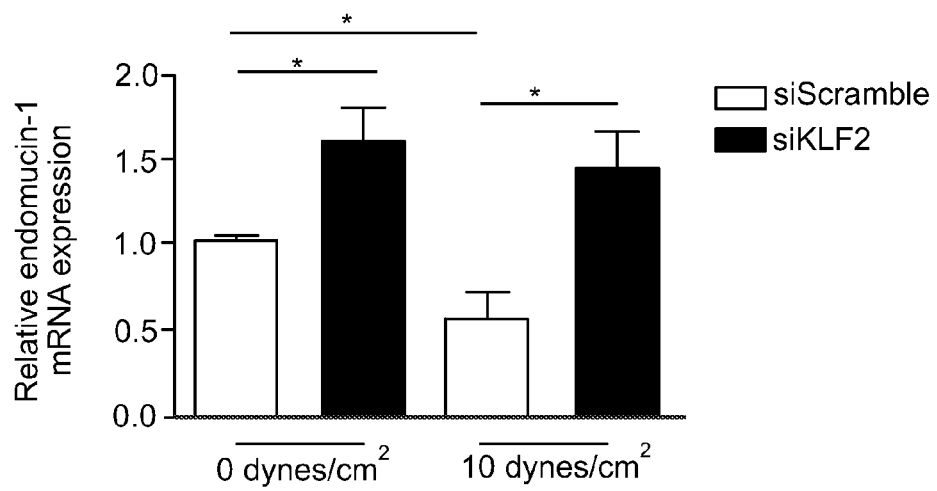

HUVECs were seeded in 6-well culture dishes and exposed to shear stress for 24 hr. EMCN-1 was down regulated in HUVEC by high shear stress of 10 dyne/cm$^2$ compared to static determined by mRNA and cell surface biotinylation, respectively (FIG. 5A). Inset is a representative gel illustrating decreased biosynthesis of EMCN-1 by shear stress-induced HUVEC compared to static control cells as measured by western blot. Venular-like shear stress of 1.5 dynes/cm$^2$ had no effect on mRNA and cell surface protein levels. Inset shows representative gel of EMCN-1 biosynthesis in HUVEC exposed to venular shear stress compared to static controls. FIG. 5C shows the results of real-time PCR analysis of EMCN-1 in Ad-Ctrl vs. Ad-KLF-2, Ad-KLF4 or Ad-KLF2/KLF4 infected HUVEC. FIG. 5D shows the results of real-time PCR analysis of EMCN-1 in response to siRNA oligonucleotides directed against KLF2 for 48 hr followed by exposure to static or flow conditions for an additional 24 hr. Relative expression of EMCN-1 was measured by real-time PCR and normalized to GAPDH mRNA levels. The amount of cDNA was normalized using GAPDH levels and quantified using a standard curve for EMCN-1. Relative cell surface expression of EMCN-1 was normalized to static controls. Biotinylation results represent one experiment performed in triplicate. *$p<0.05$, **$p<0.01$.

Thus, EMCN-1 is regulated by shear stress and is mediated by KLF2. Specifically, EMCN-1 mRNA expression and surface localization was optimal in HUVEC subjected to low shear stress conditions, while high shear stress down regulated EMCN-1.

EXAMPLE 3

Knockdown of EMCN-1 in HUVEC Leads to an Increase in Neutrophil-Endothelial Cell Interactions Neutrophil-endothelial cell interactions were studied under laminar flow in a parallel plate flow chamber. Confluent human umbilical vein endothelial cells (HUVEC) monolayers were grown on 25-mm glass cover slips coated with fibronectin. Neutrophils suspended at a concentration of 0.5× $10^6$ cells/ml were sheared across the HUVEC monolayer at 1.5, 1.0, 0.75, and 0.5 dyne/cm$^2$. These shear stresses mimic the biological shear stress range found in post-capillary veins.

Figure 6A:
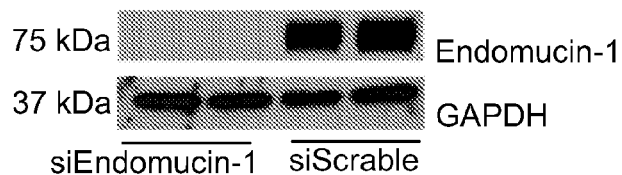
FIG. 6 is a series of bar charts, line graphs, and photomicrographs showing that knockdown of EMCN-1 in HUVEC leads to an increase in neutrophil-endothelial cell interactions. HUVEC seeded at 50% confluence were transfected with siRNA oligonucleotides targeted against EMCN-1. Analysis was performed 48 hr after transfection. (A-B) siRNA led to a more than 80% knockdown of EMCN-1 as determined by western blot in HUVEC. (C) Flow studies revealed that at shear stresses of 1.0, 0.75, and 0.5 dyn/cm$^2$, there was greater than 6-fold increase in adhesion of neutrophils compared to scramble treated HUVEC. (D) Freeze-frame of neutrophils interacting with siScramble and siEMCN-1 transfected HUVEC. (E) Knockdown of EMCN-1 did not alter the expression of pro-adhesive molecules, E-selectin, VCAM-1, or ICAM-1, as measured by FACS. (F) Neutralizing antibody to LFA-1 reverses cell-cell interactions in siEMCN-1 treated HUVEC at all shear stress studied. Data in A and E represent one of the three independent experiments performed. Values for siRNA are expressed as mean+/−SEM, and results are representative of three independent experiments. In C and F results are representative of two to three human donor and flow experiment performed in triplicate, mean+/−SEM. *P<0.05, P<0.01, *P<0.001 compared with scramble treated HUVEC. (G) Knockdown of EMCN-1 did not alter the expression of pro-adhesive molecules, E-selectin, VCAM-1, or ICAM-1, as measured by FACS. (H) Firm adhesion studies revealed that at a shear stress of 0.5 dyn/cm$^2$ there was a 6-fold increase in adhesion of neutrophils compared to scramble treated HUVEC. (I) The number of rolling neutrophils increased 3-fold compared to scramble controls in low shear stress conditions. Results represents data collected from three human subjects with flow assays performed in duplicate. *P<0.05, P<0.01, *P<0.001 compared with control cultures.
Figure 6B:
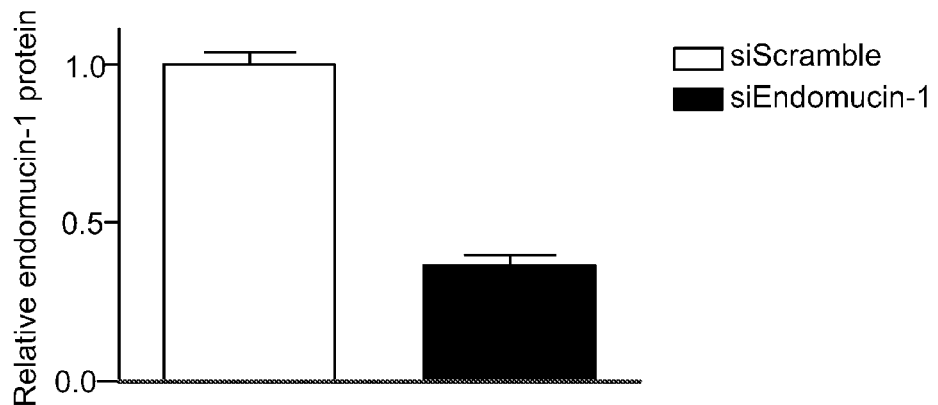
Figure 6C:
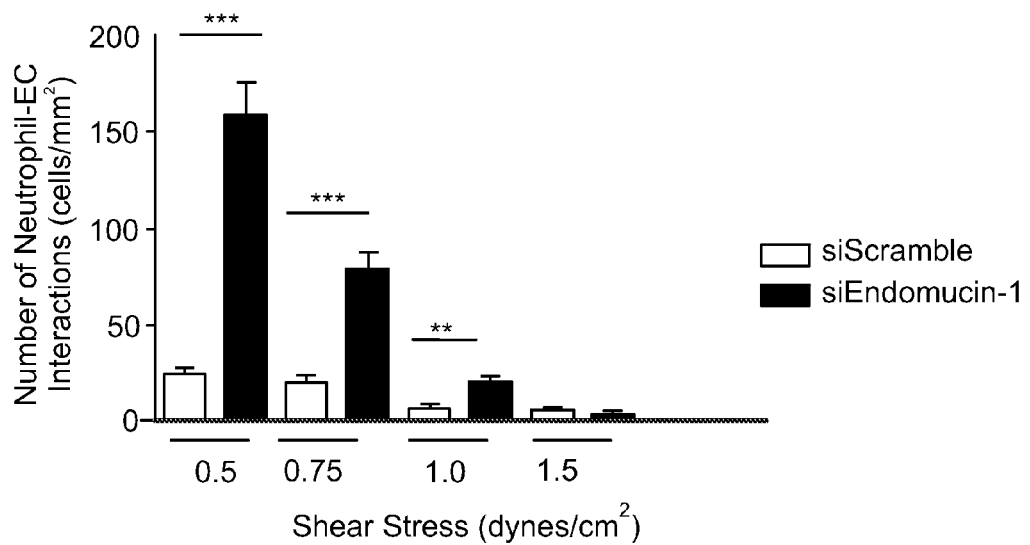

HUVEC seeded at 50% confluence were transfected with siRNA oligonucleotides targeted against EMCN-1. Analysis was performed 48 hr after transfection. siRNA led to a more than 80% knockdown of EMCN-1 as determined by western blot in HUVEC (FIGS. 6A and 6B). Knockdown of EMCN-1 by HUVEC in vitro with siRNA (FIG. 6B) led to a 6-fold increase in neutrophil adhesion on HUVEC (FIG. 6C) at low shear stringency of 0.5 and 0.75 dynes/cm$^2$, and 2.5-3 fold increase at higher shear flow whereas the scrambled control siRNA had no effect. These data indicate that in the non-inflamed (resting) state, EMCN-1 blocks neutrophil adhesion.

Figure 6D:
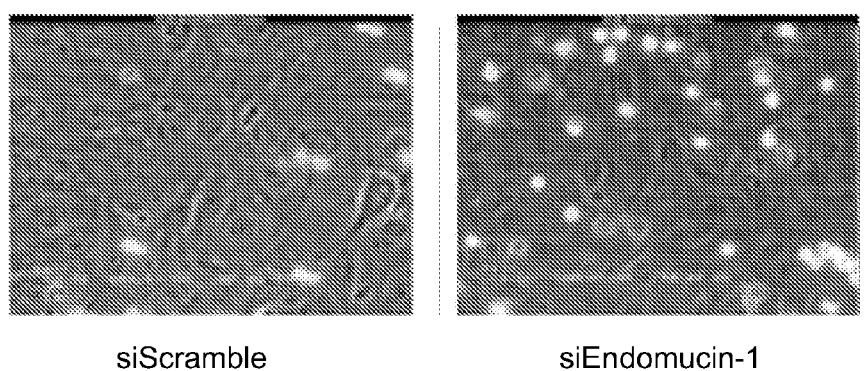
Figure 6E:
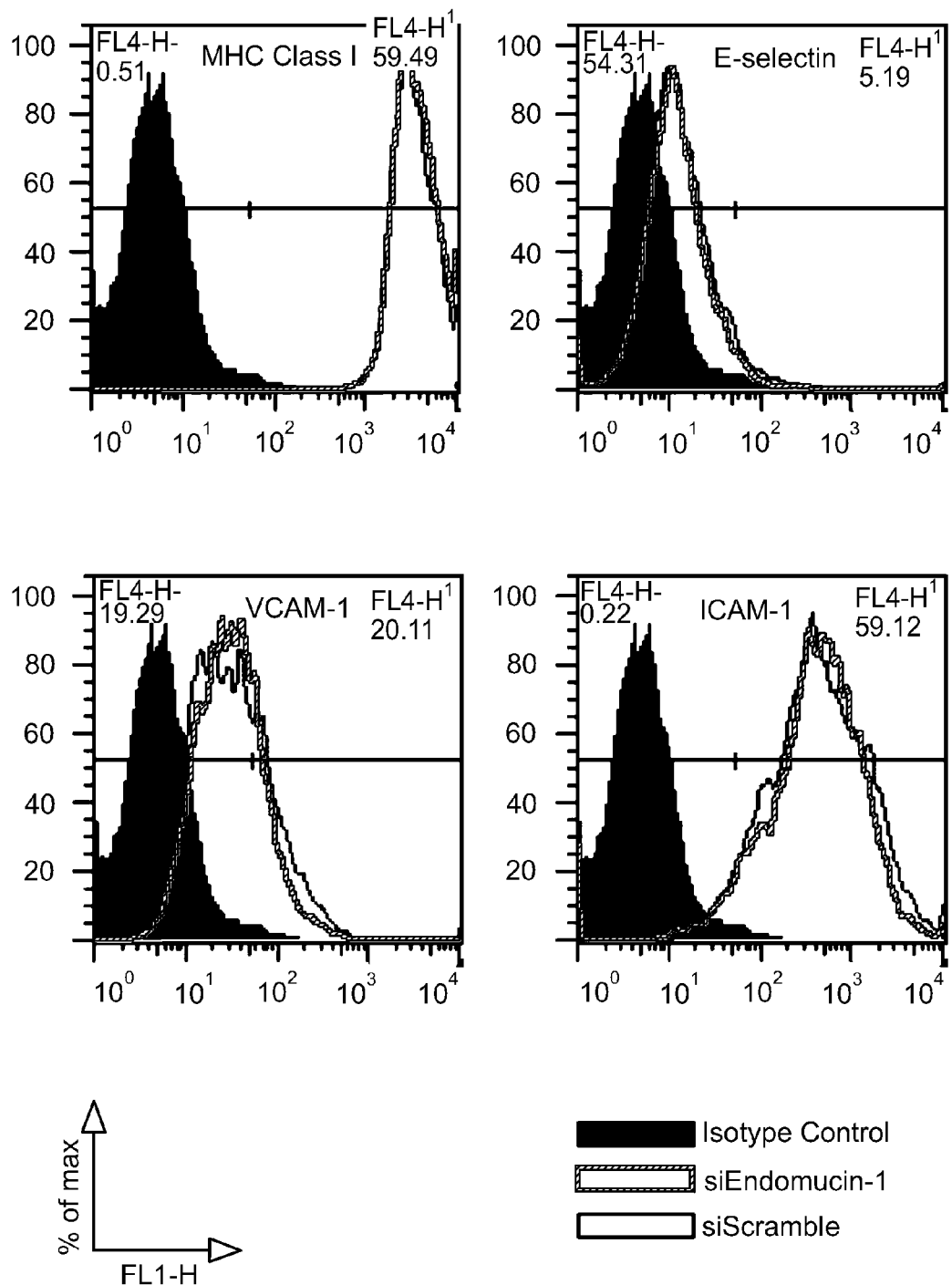

The photomicrograph in FIG. 6D shows a freeze-frame of neutrophils interacting with siScramble and siEMCN-1 transfected HUVEC. FIG. 6E shows that knockdown of EMCN-1 did not alter the expression of pro-adhesive molecules, E-selectin, VCAM-1, or ICAM-1, as measured by FACS.

Figure 6F:
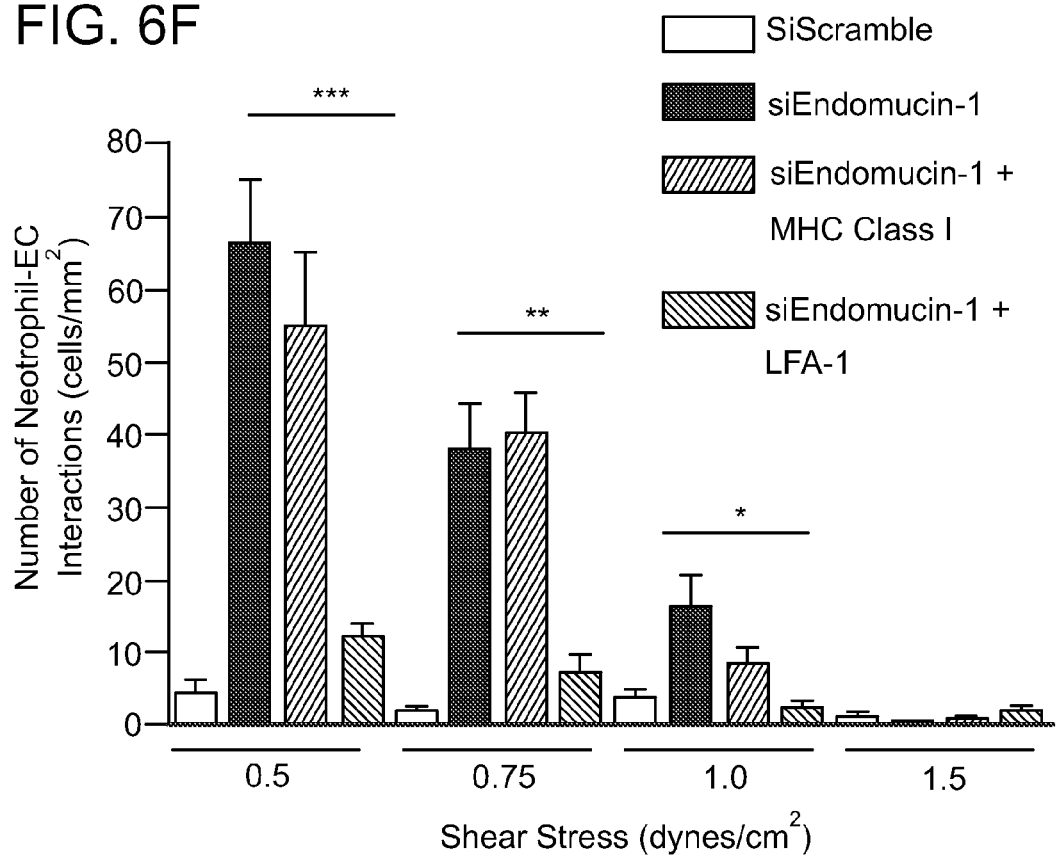
Figure 6G:
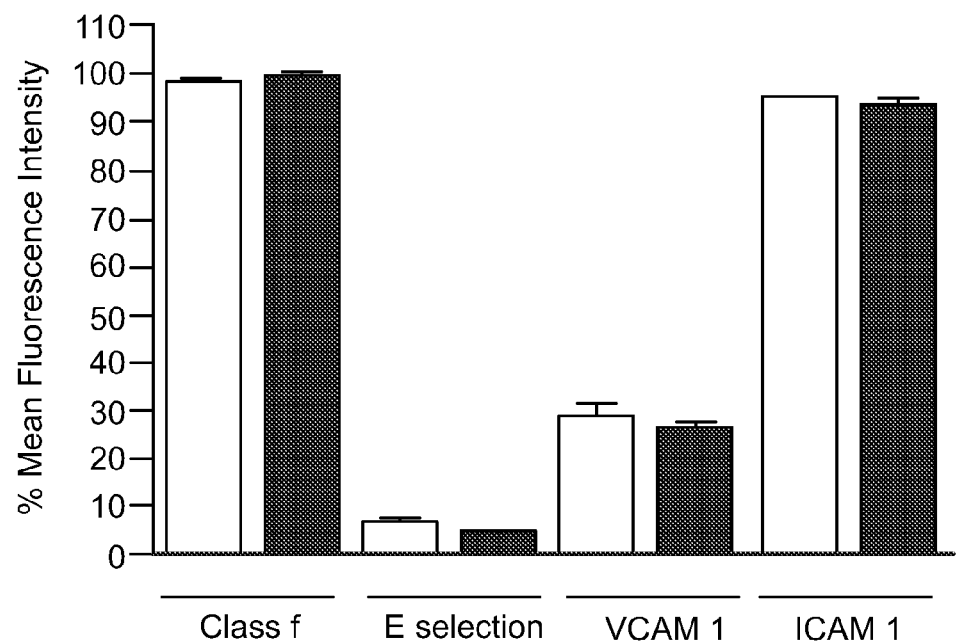
Figure 6H:
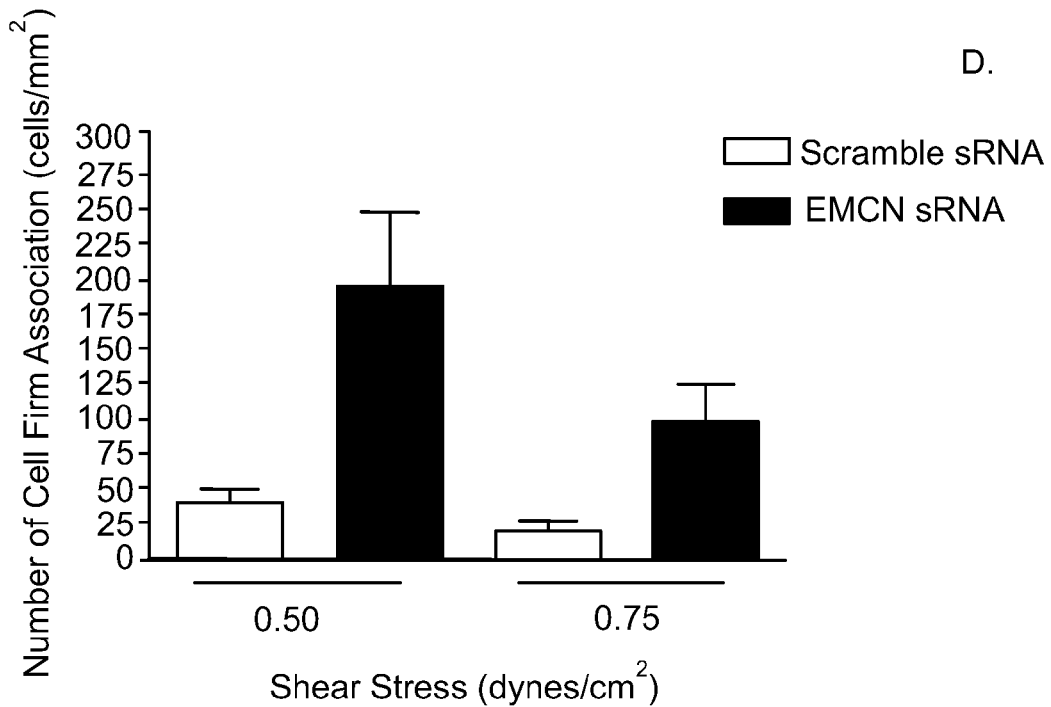
Figure 6I:
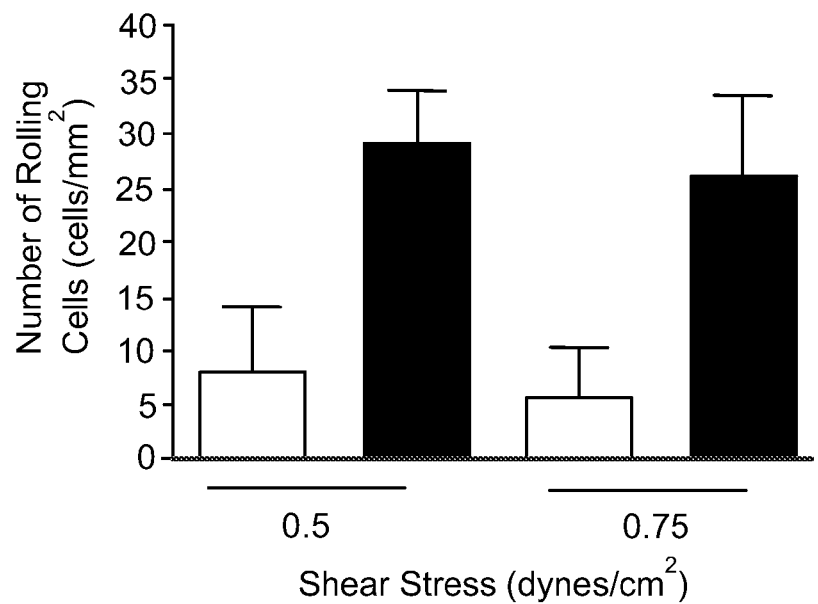

To determine which adhesion molecule is playing a role in cell-cell interactions after EMCN-1 knockdown, the expression of E-selectin, ICAM-1 or VCAM in HUVEC was examined using FACS. There was no change in adhesion molecule expression before and after siRNA treatment (FIG. 6G). Firm adhesion studies revealed that at a shear stress of 0.5 dyn/cm$^2$ there was a 6-fold increase in adhesion of neutrophils compared to scramble treated HUVEC (FIG. 6H). The number of rolling neutrophils increased 3-fold compared to scramble controls in low shear stress conditions (FIG. 6I).

As described below, the down regulation of EMCN-1 on the endothelial surface enables the neutrophils to bind to constitutively expressed leukocyte adhesion molecules. Using FACS, it was demonstrated that ICAM-1 was constitutively expressed at higher levels on the surface of HUVEC compared to E-selectin and VCAM. ICAM-1 was identified as the adhesion molecule mediating neutrophil adhesion in the absence of EMCN-1. To determine if ICAM-1 was an important adhesion molecule, neutrophils were incubated with blocking antibody to β2 integrin (i.e., LFA), which is a binding partner of ICAM-1. These neutrophils were then sheared across HUVEC monolayers in which EMCN-1 has been knocked down (FIG. 6F). A reversal in neutrophil binding was found in all shear stresses examined indicating that knockdown of EMCN-1 leads to neutrophil arrest on the endothelium through a mechanism that involves cell surface ICAM-1.

Thus, knockdown of EMCN-1 in HUVEC lead to an increased number of human neutrophil-endothelial cell interactions compared to scramble, in an in vitro parallel plate flow chamber assay, while removal of the EMCN-1 barrier in the glycocalyx produced a pro-adhesive cell surface.

EXAMPLE 4

TNF-Alpha Suppresses EMCN-1 Expression while Increasing Pro-Adhesive Molecules

Figure 7A:
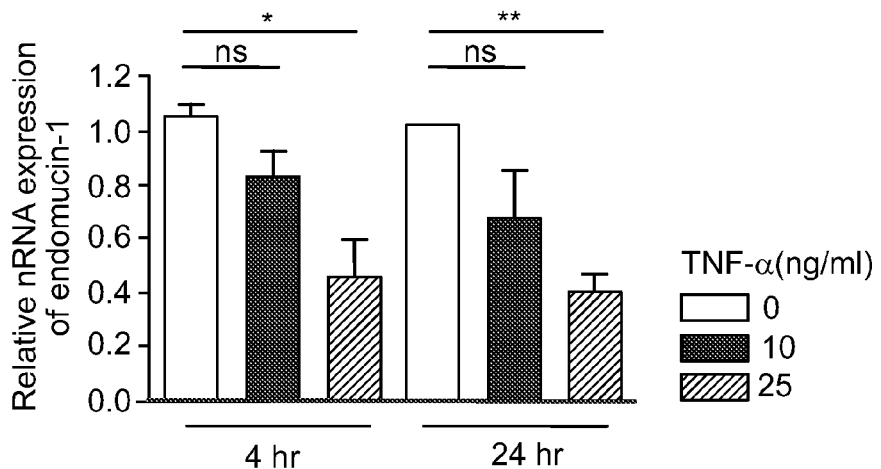
FIG. 7 is a series of bar charts, line graphs, and photomicrographs showing TNF-alpha suppresses EMCN-1 expression while increasing pro-adhesive molecules. TNF-alpha (10 and 25 ng/ml) treatment of confluent HUVEC down-regulated EMCN-1 mRNA expression (A) and cell surface protein (B-C) EMCN-1, after 4 and 24 hr, as determined by quantitative real time PCR (qRT-PCR) and cell surface biotinylation, respectively. Relative expression of EMCN-1 measured by real-time PCR and normalized to GAPDH mRNA levels (D). TNF-alpha treatment led to an up-regulation of pro-adhesive molecules, VCAM-1, ICAM-1, and E-selectin, as determined by FACS. Data is plotted as % of max versus FL4-H (fluorescence). (E) IHC of EMCN-1 (green), ICAM-1 (red) in confluent untreated HUVEC. Treatment with 10 ng/ml of TNF-alpha for 24 hr, results in a down-regulation of surface associated EMCN-1 (green) and up-regulation of ICAM-1 (red). White arrows represent areas of EMCN-1 negative cells. Results in D represent one of three independent experiments performed. Values are expressed as mean+/−SEM, and results are representative of three independent experiments. (F) whole cell of EMCN-1, after 4 and 24 hr, as determined by cell surface biotinylation and western blotting, respectively.
Figure 7B:
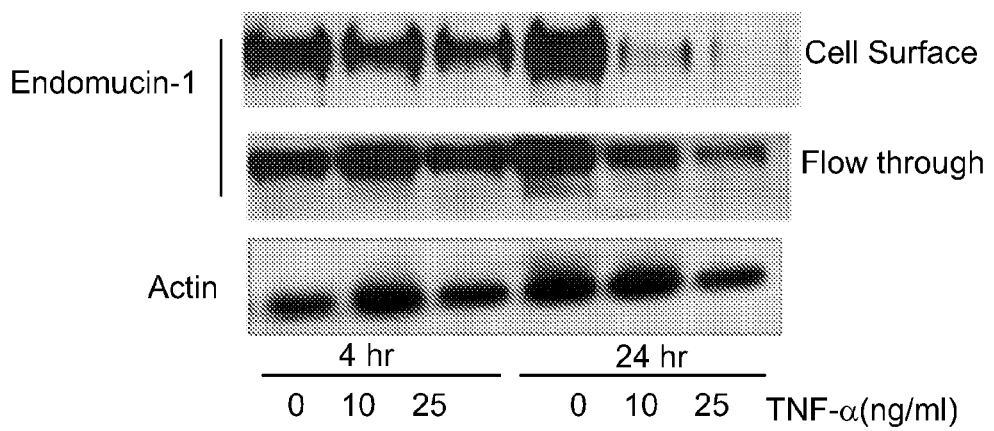
Figure 7C:
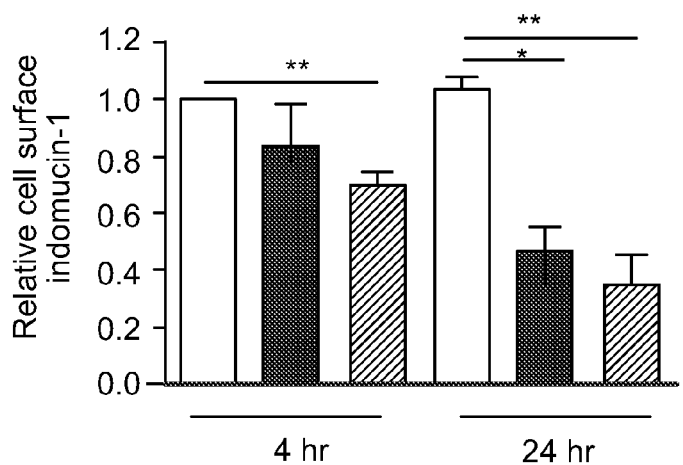

Treatment of HUVEC with TNF-alpha, a pro-inflammatory cytokine, led to the down regulation of EMCN-1 mRNA expression (FIG. 7A). Biotinylation of HUVEC surface proteins following TNF-alpha treatment revealed that cells treated for 24 hr with 25 and 10 ng/ml TNF-alpha had virtually no cell surface EMCN-1 (FIGS. 7B and C). As expected, TNF-alpha treatment was also associated with an increase in pro-adhesive molecules, VCAM-1, ICAM-1, and E-selectin, as determined by FACS (FIG. 7D).

Figure 7E:
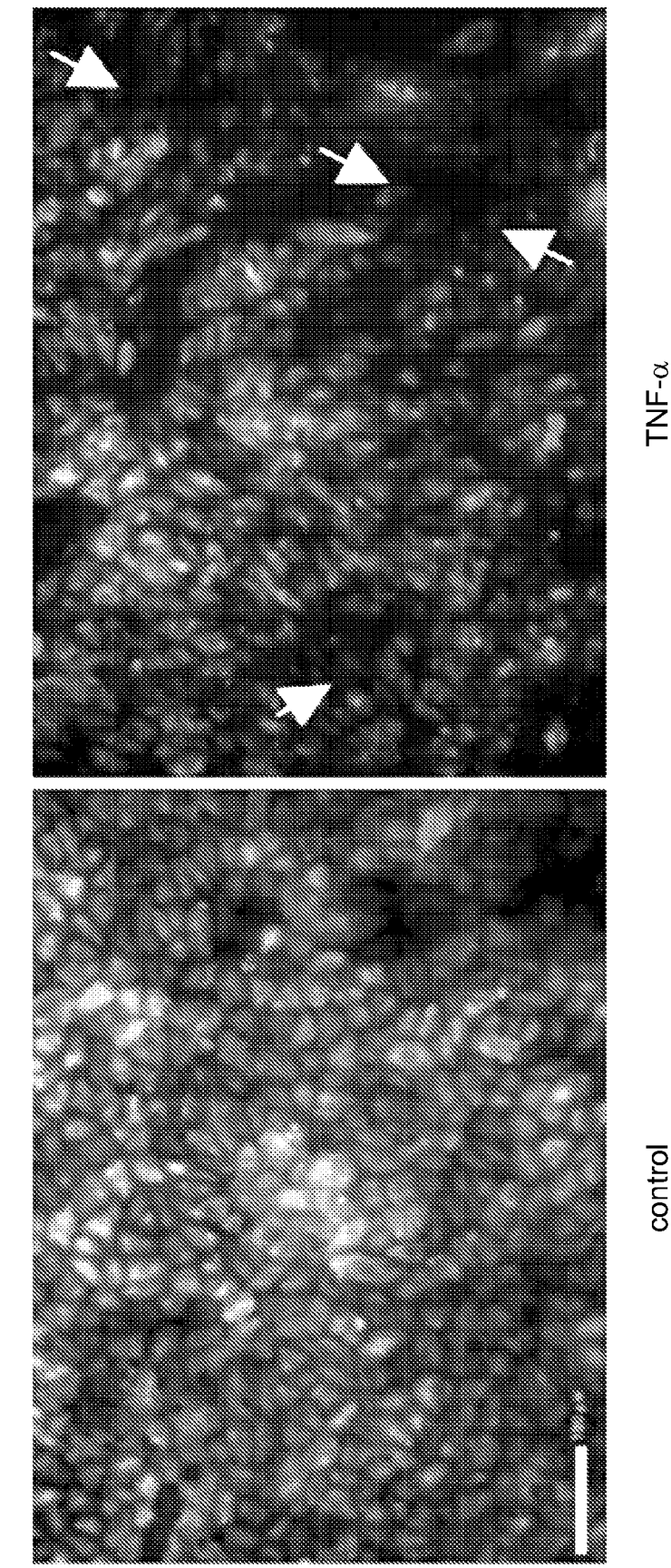
Figure 7F:
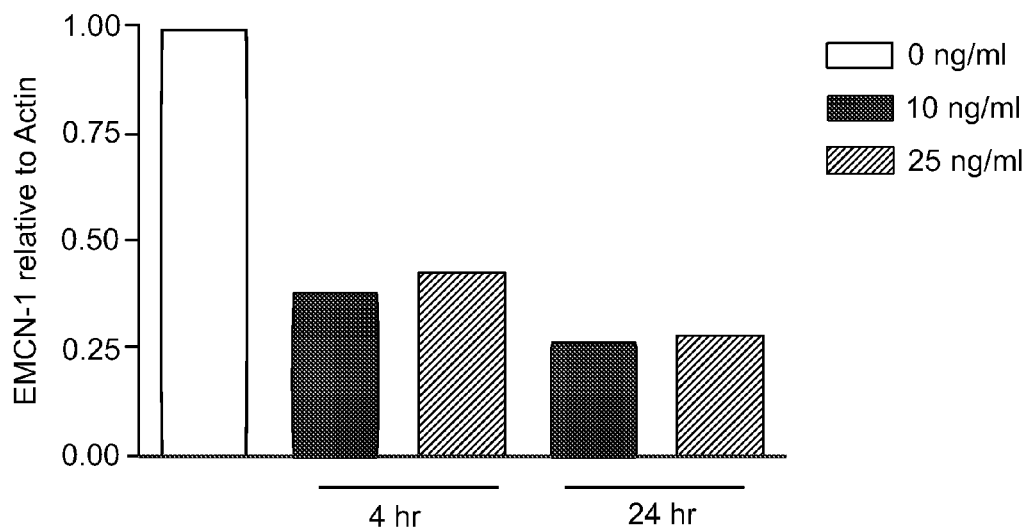

FIG. 7E shows immunohistochemistry staining of EMCN-1 (green) and ICAM-1 (red) in confluent untreated (control) HUVEC. Treatment with 10 ng/ml of TNF-alpha for 24 hr, resulted in a down-regulation of surface associated EMCN-1 (green) and up-regulation of ICAM-1 (red). White arrows represent areas of EMCN-1 negative cells. FIG. 7F shows relative ECM-1 expression in whole cell lysate of EMCN-1, after 4 and 24 hr, as determined by cell surface biotinylation and western blotting, respectively.

Thus, the pro-inflammatory cytokine, TNF-alpha, down-regulated EMCN-1 mRNA expression and cell surface protein in HUVEC, and up-regulated the pro-adhesive molecules E-selectin, VCAM-1, and ICAM-1. EMCN-1 overexpression in HUVEC protects cells from TNF-alpha activation.

EXAMPLE 5

Overexpression of EMCN-1 Blocks Neutrophil Adhesion to TNF-Alpha Activated HUVEC and In Vivo To determine the contribution of EMCN to neutrophil adhesion to activated endothelium, EMCN-1 was over expressed in HUVEC at a multiplicity of infection (MOI) of 6 using an adenovirus expressing full-length mouse EMCN-1, followed by treatment with TNF-alpha (10 ng/ml, 24 hr).

Figure 8A:
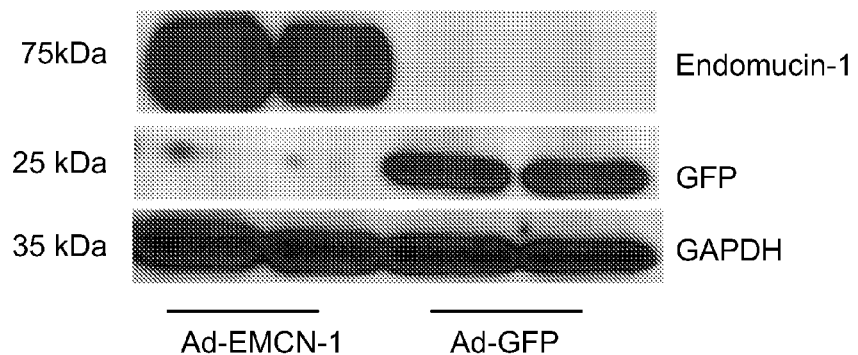
FIG. 8 is a series of bar charts, a photomicrograph, and a dot plot showing that over expression of EMCN-1 protects endothelial cells from neutrophil adhesion induced by treatment with TNF-alpha. (A) Sub-confluent HUVEC were infected with adenoviruses expressing green fluorescent protein (Ad-GFP) or EMCN-1 (Ad-EMCN-1) at a multiplicity of infection (MOI) 6 and protein biosynthesis of mouse EMCN-1 and GFP was determined after 48 hr of infection by western blot to confirm over expression. TNF-alpha, 10 ng/ml, treatment of HUVEC over expressing EMCN-1 led to a moderate reduction of mouse EMCN-1 as determined by whole cell lysate analysis. (B) FACS analysis of pro-adhesive molecules, E-selectin, VCAM-1, and ICAM-1 are unaffected by over expression of Ad-GFP and Ad-EMCN-1 in HUVEC after 48 hr infection with adenovirus. (C) Flow studies at shear stress of 1.5, 1.0, 0.75, and 0.5, revealed that TNF-alpha treatment of cells over expressing of mouse EMCN-1 led to a reduced total number of neutrophil-endothelial interactions compared to controls. (D) EMCN-1 over expression did not prevent transmigration of neutrophils that adhered to TNF-alpha treated HUVEC surfaces transfected with Ad-EMCN-1 compared to control Ad-GFP transfected cells. Results in a, b, and c, represent one of three independent experiments performed. In c and d results are representative of three human donor experiments performed for flow and transmigration studies, with each independent study performed in triplicate or duplicate, respectively. Results represent mean+/−SEM. *P<0.05, P<0.01, *P<0.001 compared with Ad-GFP HUVEC.

Protein biosynthesis of mouse EMCN-1 and GFP was determined after 48 hr of infection by western blot to confirm over expression (FIG. 8A). TNF-alpha, 10 ng/ml, treatment of HUVEC over expressing EMCN-1 led to a moderate reduction of mouse EMCN-1 as determined by whole cell lysate analysis. FACS analysis showed that pro-adhesive molecules, E-selectin, VCAM-1, and ICAM-1 were unaffected by over expression of Ad-GFP and Ad-EMCN-1 in HUVEC after 48 hr infection with adenovirus (FIG. 8B).

Figure 8C:
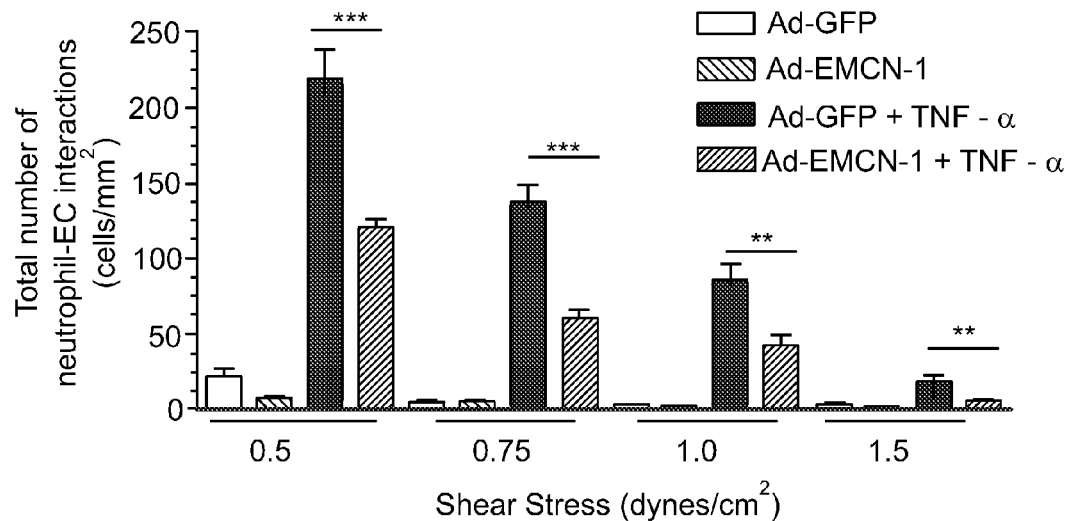

The effect of EMCN-1 over expression on the ability of neutrophils to adhere to the HUVEC was examined in the flow adhesion assay. At all shear stress studied over expression of EMCN-1 in the presence of TNF-alpha was able to protect the cells from neutrophil adhesion compared to control cells (FIG. 8C). At the lower shear stresses of 0.5 and 0.75 dyne/cm$^2$, there was an approximate 3-fold decrease in neutrophil adhesion. This decrease in adhesion illustrates EMCN-1 as a potent therapeutic molecule that can protect the endothelium from neutrophil mediated adhesion, and thus inflammation.

Figure 8D:
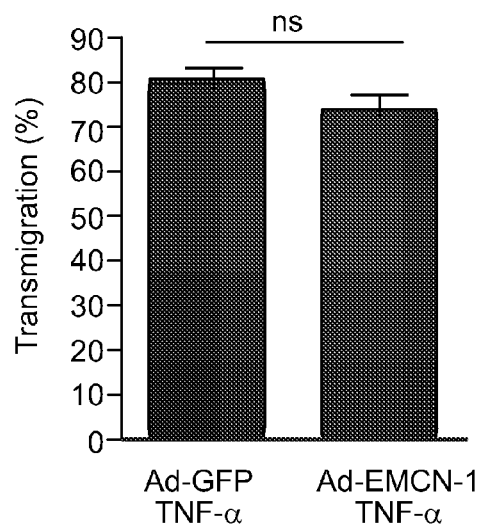

EMCN-1 over expression did not prevent transmigration of neutrophils that adhered to TNF-alpha treated HUVEC surfaces transfected with Ad-EMCN-1 compared to control Ad-GFP transfected cells (FIG. 8D).

Figure 9C:
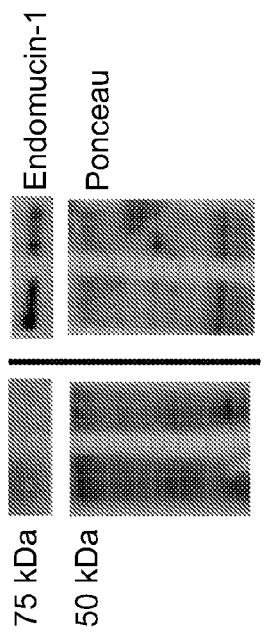
FIG. 9 is a series of blots and a bar chart demonstrating that TNF-alpha suppresses EMCN-1 protein expression in vivo. (A-B) Intravitreal injection of TNF-alpha (n=3) and saline (n=3) was performed in BL6 mice. After 2 and 24 hr, protein lysates from the anterior segment (AS, ciliary body and iris) were collected. Western blotting of AS lysates revealed a decreased expression of EMCN-1 in eyes treated with TNF-alpha compared to saline injected controls. (C-D) Over expression of EMCN-1 in the eye was accomplished by intravitreal injection of Ad-EMCN-1. After one week, protein lysates from neural retina and ciliary body and anterior segment were collected to confirm over expression EMCN-1, respectively.
Figure 9D:
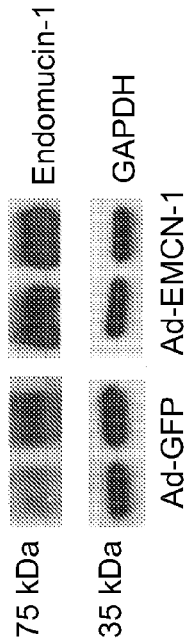
Figure 9A:
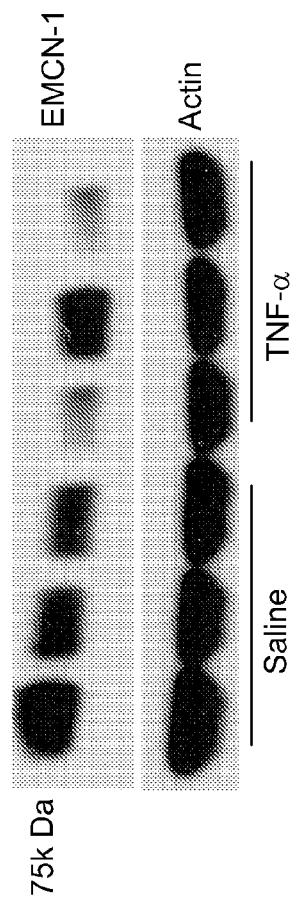
Figure 9B:
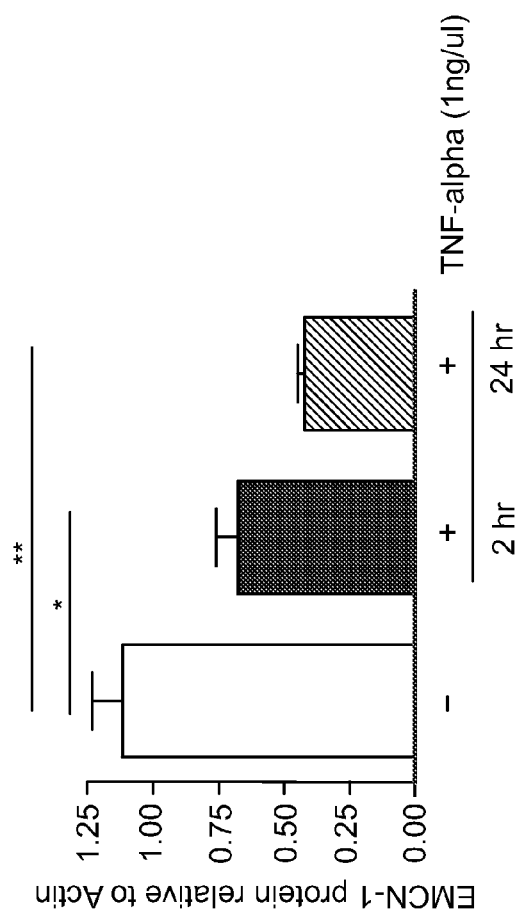

As discussed above, EMCN-1 is highly expressed in the vascular beds of the iris, ciliary body, neural retina, and the choriocapillaris. To determine if the down regulation of EMCN-1 under inflammatory conditions can be replicated in vivo, 1 ng/µl of TNF-alpha was intravitreally injected into the mouse eye. After 2 and 24 hrs, the anterior segment was collected and processed for western blotting (FIG. 9A). As seen in FIG. 9B, the relative expression of EMCN-1 in the anterior segment was down regulated by TNF-alpha after 2 hrs and by 50% after 24 hrs. Adenovirus expressing GFP and EMCN-1 was intravitreally injected and after one week the neural retina and ciliary body were collected for western blotting to confirm the over expression of EMCN-1 in the retina (FIGS. 9C and 9D).

Figure 10A:
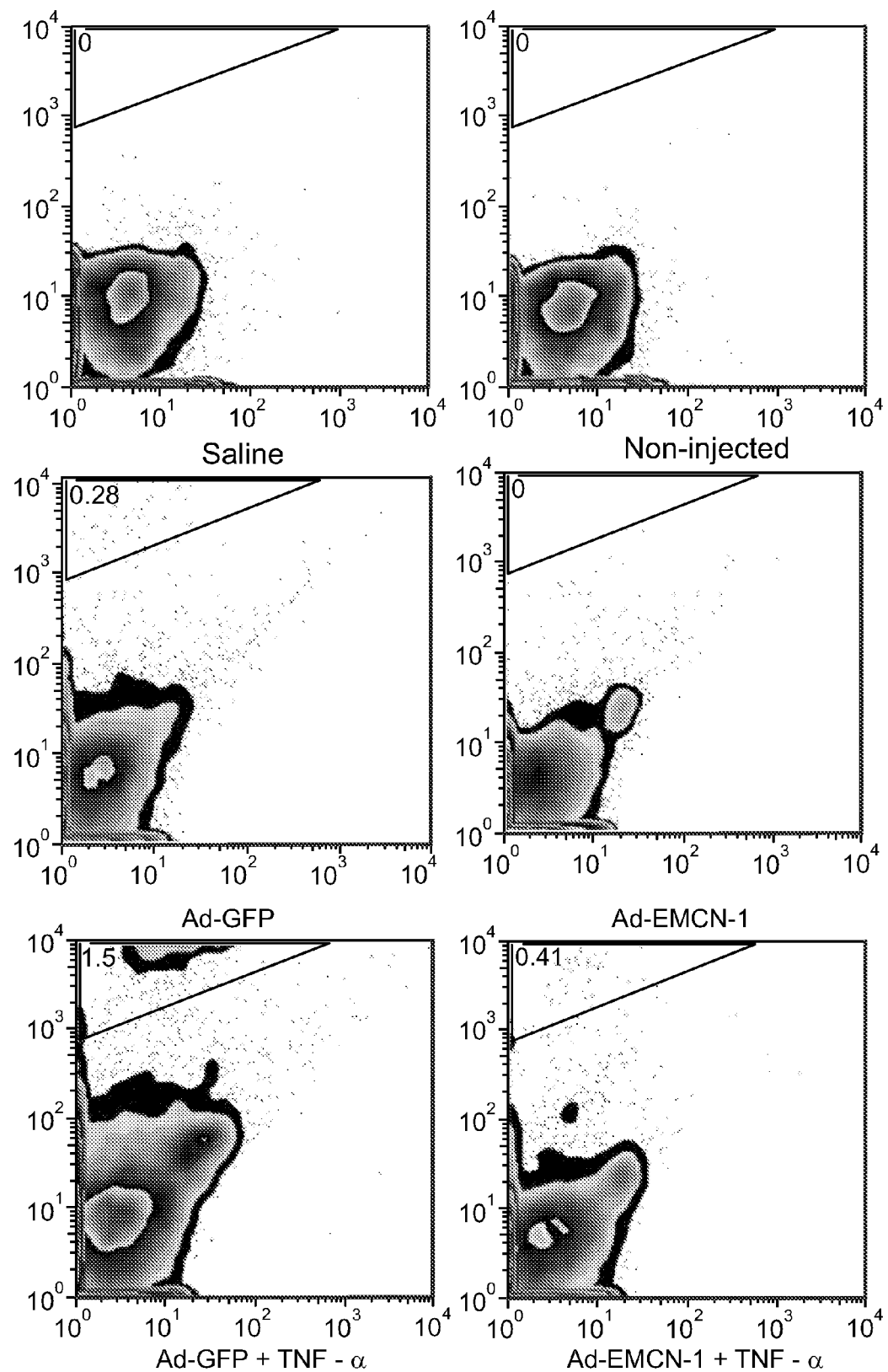
FIG. 10 is a histogram and a bar chart showing that over expression of EMCN-1 in the neural retina and ciliary body protects cells from TNF-alpha induced infiltration of CD45+ cells. After one week of infection with Ad-GFP and Ad-EMCN-1, mice were treated with a 20 ng/ml dose of TNF-alpha intravitreally for 24 hrs. After 24 hrs, neural retina and ciliary body were dissected and dissociated into a single cell suspension using a papain kit. FACS analysis on the suspended cells was used to probe for CD45+ infiltrates (A) Representative histogram from uninjected eyes, saline injected eyes, Ad-GFP, Ad-EMCN-1, Ad-GFP+TNF-alpha, and Ad-EMCN-1+TNF-alpha infected mice (n=12). Data is plotted as PE-Cy5-A versus FITC-A representative of Cy5 positive CD45+ cells and GFP positive infected cells, respectively. Gates were drawn around cells highly expressing fluorescent marker Cy5-A. (B) Analysis of FACS data, histogram of total number of CD45+ cells versus saline injected control, Ad-GFP, Ad-GFP+TNF-alpha, Ad-EMCN-1, and Ad-EMCN-1+TNF-alpha. Results were calculated from total number of Cy5+ cells subtracted total number of Cy5+ cells in IgG Isotype controls. There was no detectable CD45+ in noninjected controls. ***P<0.001 compared with Ad-GFP+TNF-alpha treated mice with Ad-EMCN-1+TNF-alpha treated mice.
Figure 10B:
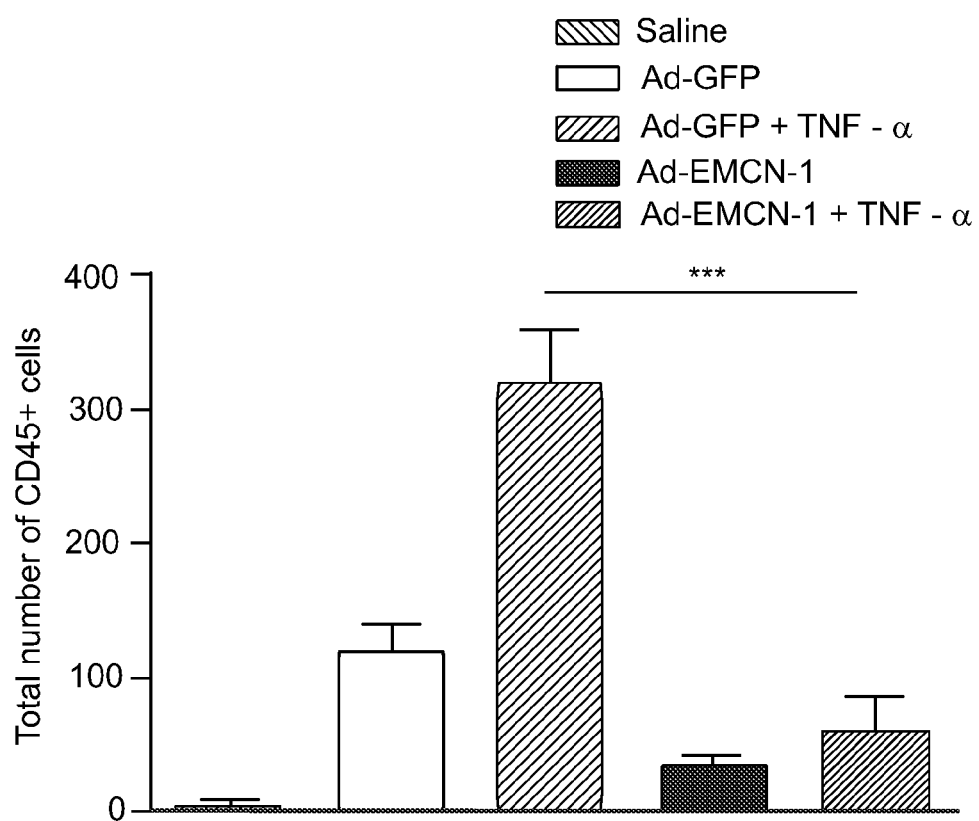

After one week of gene therapy, mice were intravitreally injected with 20 ng/µl of TNF-alpha. A higher dose of TNF-alpha was used to ensure optimal infiltration of CD45+ cells into the neural retina and ciliary body. After a total of 8 days of treatment, the neural retina and ciliary body were dissected and treated with papain to dissociate the tissue into a single cell suspension. Cells were then treated with monoclonal antibody to CD45+ and then processed by FACS (FIG. 10A). Infiltration of CD45+ cells in mice injected with adenovirus GFP control was statistically higher compared mice over expressing EMCN-1 indicating that EMCN-1 over expression suppresses off-target affects of the adenovirus vector (FIG. 10B). Furthermore, an approximate 6-fold decrease in CD45+ cells was identified in the neural retina and ciliary body with mice over expressing EMCN-1 and treated for 24 hrs with TNF-alpha compared to GPF treated mice. This finding supports the use of EMCN-1 as a molecule that can regulate adhesion and infiltration of immune derived monocytes in vivo.

Thus, neutrophil adhesion to the activated HUVEC surface was significantly down regulated. Intravitreal injection of TNF-alpha after 24 hrs down-regulates anti-adhesive glycoprotein EMCN-1, while overexpression of EMCN-1 in the eye protects neural retina and ciliary body from TNF-alpha activation and recruitment of CD45+ cells.

EXAMPLE 6

Figure 11B:
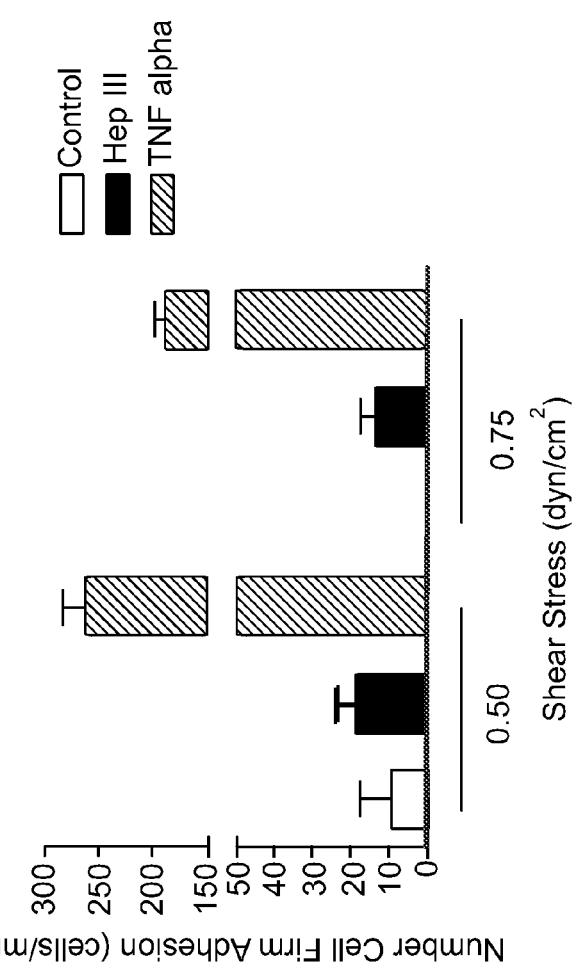
FIG. 11 is a series of bar charts demonstrating that removal of heparin sulfate barrier has a modest effect on neutrophil-endothelial cell interactions compared to EMCN-1 KD. Adhesion studies reveal the relative contribution of the glycocalyx in cell-cell interactions, (A) firm adhesion and (B) rolling. Under physiological flow conditions, there was minimal neutrophil adhesion onto the HUVEC monolayer. After pre-treatment with heparinase III (15 mU/mL, 2 hr), a 5-fold increase in the number of rolling cells was observed at 0.5 dyn/cm$^2$ compared to control. TNF-alpha (25 ng/ml, 24 hr) lead to an increased number of cells firmly adhering to the HUVEC monolayer. These studies represent neutrophils collected from one human donor and flow experiments were performed in triplicate under each condition studied.
Figure 11A:
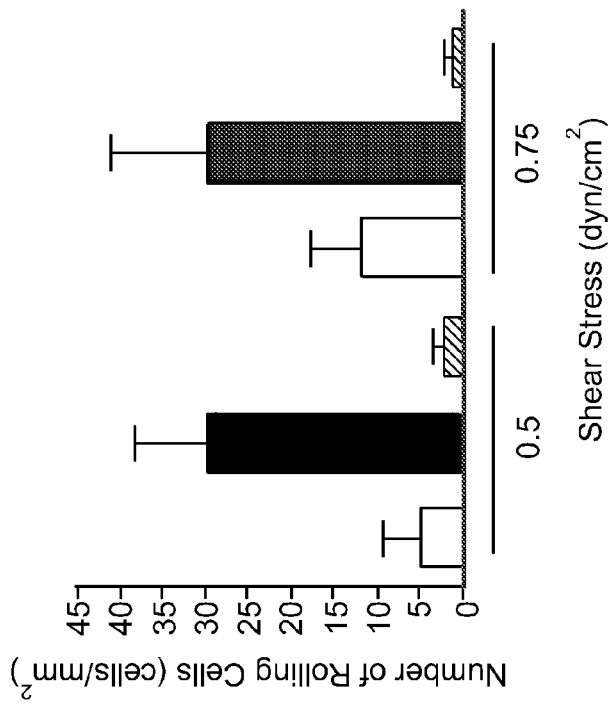

Removal of Heparan Sulfate Barrier has a Modest Effect on Neutrophil-Endothelial Cell Interactions Adhesion studies revealed the relative contribution of the glycocalyx in cell-cell interactions: firm adhesion (FIG. 11A) and rolling (FIG. 11B). Under physiological flow conditions, there was minimal neutrophil adhesion onto the HUVEC monolayer. After pre-treatment with heparinase III (15 mU/mL, 2 hr), a 5-fold increase in the number of rolling cells was observed at 0.5 dyn/cm$^2$ compared to control. TNF-alpha (25 ng/ml, 24 hr) lead to an increased number of cells firmly adhering to the HUVEC monolayer.

Figure 12A:
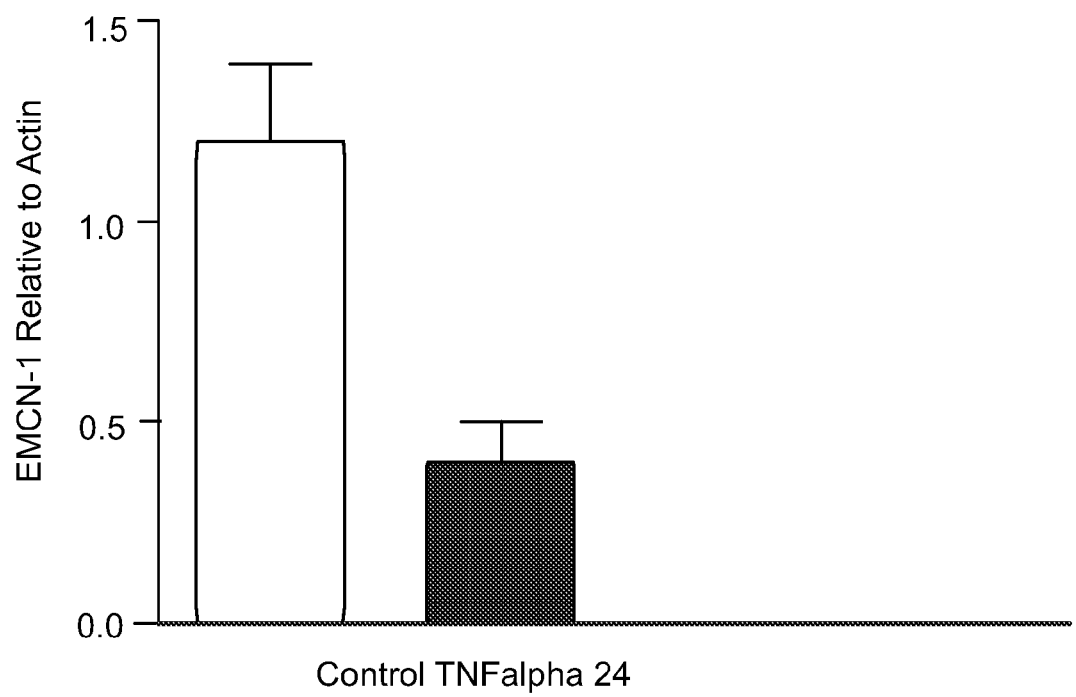
FIG. 12 is a bar chart and a photomicrograph showing that EMCN-1 is regulated by inflammation in the eye. Intravitreal injection of TNF-alpha down-regulates EMCN-1 in the anterior segment of the mouse eye. (A) Intravitreal injection of TNF-alpha (n=3) and saline (n=3) was performed in BL6 mice. After 24 hr, protein lysates from the anterior segment (AS, ciliary body and iris) were collected. Western blotting of AS lysates revealed a decreased expression of EMCN-1 in eyes treated with TNF-alpha compared to saline injected (B) IF of EMCN-1 in the ciliary body, red (scale bar 56 µm).
Figure 12B:
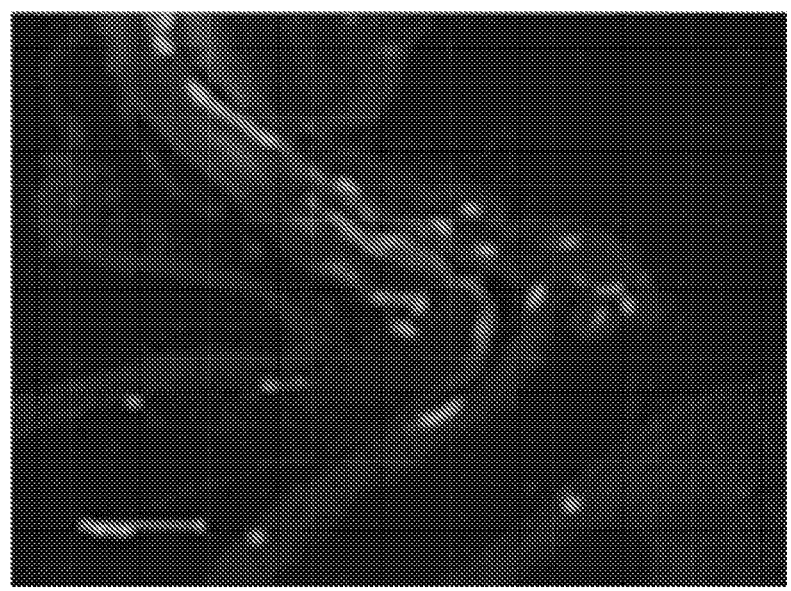

As shown in FIG. 12, intravitreal injection of TNF-alpha down-regulates EMCN-1 in the anterior segment of the mouse eye. Intravitreal injection of TNF-alpha (n=3) and saline (n=3) was performed in BL6 mice. After 24 hr, protein lysates from the anterior segment (AS, ciliary body and iris) were collected. Western blotting of AS lysates revealed a decreased expression of EMCN-1 in eyes treated with TNF-alpha compared to saline injected eyes. Immunofluorescence of EMCN-1 in the ciliary body (red) is shown in FIG. 12B.

Figure 13A:
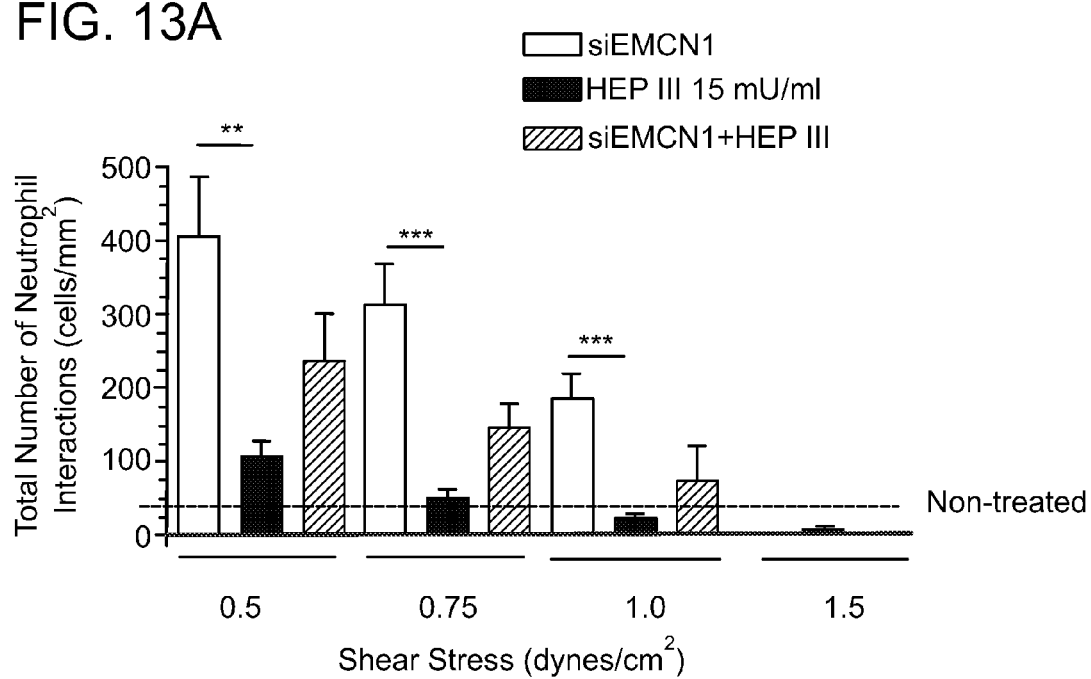
FIG. 13 is a bar chart and a photomicrograph showing the relative contribution of the glycocalyx in neutrophil-endothelial cell interactions. Treatment of HUVEC monolayer with heparinase III (15 mU/ml, 2 hr) led to a modest increase in cell-cell interactions compared to (A) EMCN-1 siRNA treated HUVEC (B) Immunofluorescence localization of heparan sulfate (red) in untreated and heparinase III-treated HUVEC. Results represent neutrophils collected from one independent human donor (performed in duplicates) and flow experiments were performed in triplicate under each condition studied, mean+/−SEM. P<0.01, *P<0.001 compared with scramble treated HUVEC or untreated HUVEC.
Figure 13B:
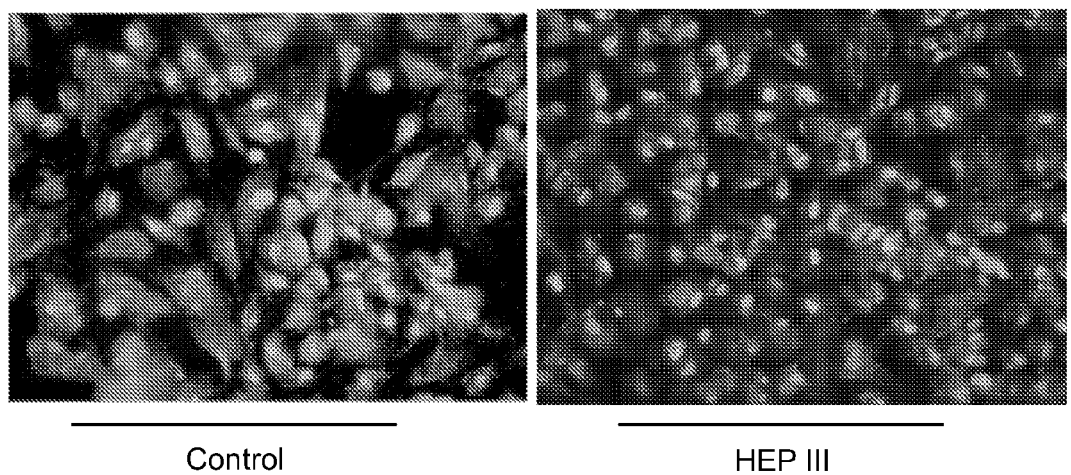

Treatment of HUVEC monolayer with heparinase III (15 mU/ml, 2 hr) led to a modest increase in cell-cell interactions compared to EMCN-1 siRNA treated HUVEC (FIG. 13A) Immunofluorescence localization of heparan sulfate (red) in untreated and heparinase III-treated HUVEC is shown in FIG. 13B.

Thus, heparinase III treatment of HUVEC lead to a modest increase in rolling neutrophils compared to control, TNF-alpha treated, and siRNA knockdown of EMCN-1. Finally, intravitreal injection of TNF-alpha after 24 hrs down-regulated anti-adhesive glycoprotein EMCN-1.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of reducing inflammation in a subject comprising:
   increasing the level of endomucin (EMCN) on endothelial cells in a tissue of said subject;
   wherein an increase in EMCN reduces the adhesion of said leukocytes to said endothelial cells in said tissue.

2. The method of claim 1, wherein a purified EMCN polypeptide is administered to said subject.

3. The method of claim 1, wherein a purified nucleic acid encoding said EMCN is administered to said subject.

4. The method of claim 2, wherein said purified EMCN polypeptide comprises the amino acid sequence of SEQ ID NO: 2.

5. The method of claim 3, wherein said purified nucleic acid encoding said EMCN comprises the sequence of SEQ ID NO: 1.

6. The method of claim 1, wherein said EMCN is human EMCN-1.

7. The method of claim 1, wherein said inflammatory disease is an ocular inflammatory disease selected from the group consisting of dry eye disease, uveitis, diabetic retinopathy, and endophthalmitis.

8. The method of claim 1, wherein said inflammatory disease is a non-ocular inflammatory disease selected from the group consisting of psoriasis, rheumatoid arthritis, inflammatory bowel disease, asthma, transplant rejection disease, vasculitis, and an autoimmune disease.

9. The method of claim 1, wherein said endothelial cells comprise vascular endothelial cells.

10. The method of claim 1, wherein said leukocyte comprises a neutrophil, an eosinophil, a basophil, a lymphocyte, a monocyte, a macrophage, or a dendritic cell.

11. The method of claim 1, wherein said adhesion is reduced at least 5%.

12. A method for reducing inflammation in a subject, the method comprising:
    injecting into a tissue a vector comprising a nucleic acid construct comprising a polynucleotide sequence for EMCN-1 operably linked to a promoter such that said EMCN-1 is over-expressed, thereby reducing inflammation is said subject.

13. The method of claim 12, wherein said vector comprises an adenovirus vector.

14. The method of claim 12, wherein overexpression of said EMCN-1 reduces the adhesion of leukocytes to endothelial cells in said subject.

15. The method of claim 12, wherein overexpression of said EMCN-1 reduces inflammatory cell infiltration.

16. The method of claim 15, wherein said inflammatory cell is a CD45+ cell.

17. The method of claim 12, wherein said adenovirus vector is injected into the eye, the skin, or a vein.

18. The method of claim 17, wherein said adenovirus vector is injected intravitreally, subcutaneously, or intravenously.

* * * * *